(12) United States Patent
Hirai et al.

(10) Patent No.: US 7,994,330 B2
(45) Date of Patent: Aug. 9, 2011

(54) METHOD FOR PRODUCING ORGANIC COMPOUND AND METHOD FOR DECOMPOSING COMPOUND HAVING DICARBOXIMIDE SKELETON

(75) Inventors: Naruhisa Hirai, Himeji (JP); Jun Kuwana, Himeji (JP)

(73) Assignee: Daicel Chemical Industries, Ltd., Sakai-Shi (JP)

( * ) Notice: Subject to any disclaimer, the term of this patent is extended or adjusted under 35 U.S.C. 154(b) by 900 days.

(21) Appl. No.: 11/885,125

(22) PCT Filed: Mar. 22, 2006

(86) PCT No.: PCT/JP2006/005691
§ 371 (c)(1),
(2), (4) Date: Aug. 27, 2007

(87) PCT Pub. No.: WO2006/103989
PCT Pub. Date: Oct. 5, 2006

(65) Prior Publication Data
US 2008/0171881 A1    Jul. 17, 2008

(30) Foreign Application Priority Data

Mar. 28, 2005 (JP) ................... 2005-091065

(51) Int. Cl.
*C07D 211/22* (2006.01)
*C07D 233/40* (2006.01)
(52) U.S. Cl. ................. 546/243; 548/263.4; 548/316.7
(58) Field of Classification Search .......... None
See application file for complete search history.

(56) References Cited

U.S. PATENT DOCUMENTS

| | | |
|---|---|---|
| 7,084,090 B2 | 8/2006 | Ishii et al. |
| 7,091,342 B2 | 8/2006 | Ishii et al. |
| 7,115,541 B2 | 10/2006 | Ishii et al. |

FOREIGN PATENT DOCUMENTS

| | | |
|---|---|---|
| JP | 8-38909 A | 2/1996 |
| JP | 9-327626 | 12/1997 |
| JP | 2002-128726 A | 5/2002 |
| JP | 2002-301376 A | 10/2002 |
| JP | 2002-308820 A | 10/2002 |
| JP | 2003-128618 A | 5/2003 |
| WO | WO-02/40154 A1 | 5/2002 |
| WO | WO-03/028884 A1 | 4/2003 |
| WO | WO-03/055600 A1 | 7/2003 |

OTHER PUBLICATIONS

Machine Translation of JP-2002-128726, May 9, 2002.
Machine Translation of JP-2002-301376, Oct. 15, 2002.
Machine Translation of JP-2002-308820, Oct. 23, 2002.

*Primary Examiner* — Zinna Northington Davis
(74) *Attorney, Agent, or Firm* — Birch, Stewart, Kolasch & Birch, LLP

(57) ABSTRACT

It is desirable to provide a method for easily removing catalyst-derived impurities from a product of a reaction by the catalysis of a compound having a dicarboximide skeleton and thereby efficiently yielding a target compound with high purity.

Disclosed is a method for producing an organic compound through a reaction of a substrate in the presence of a catalyst, the catalyst including a compound having a dicarboximide skeleton represented by following Formula (i):

[Chemical Formula 1]

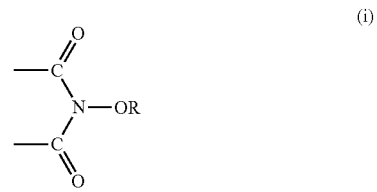

(i)

wherein R represents hydrogen atom or a hydroxyl-protecting group. The method includes the step of treating a reaction product with hot water so as to decompose and remove an impurity derived from the catalyst. The temperature of the hot water is preferably 100° C. or higher.

3 Claims, No Drawings

METHOD FOR PRODUCING ORGANIC COMPOUND AND METHOD FOR DECOMPOSING COMPOUND HAVING DICARBOXIMIDE SKELETON

TECHNICAL FIELD

The present invention relates to a method for producing an organic compound using a catalyst containing a compound having a dicarboximide skeleton, and a method for decomposing a compound having a dicarboximide skeleton.

BACKGROUND ART

When a compound having a dicarboximide skeleton, such as a cyclic imide compound or a cyclic acylurea compound, is used as a catalyst, various radical reactions satisfactorily proceed on various substrates to thereby yield a variety of useful organic compounds efficiently under mild conditions (Patent Documents 1 to 6). By oxidizing a compound having an alkyl group bonded to an aromatic ring, for example, with oxygen in the presence of this catalyst, the alkyl group is efficiently oxidized, and thus an aromatic carboxylic acid such as terephthalic acid or pyromellitic acid can be industrially efficiently produced. By oxidizing a non-aromatic cyclic hydrocarbon such as cyclohexane with oxygen in the presence of the catalyst, an alcohol, a hydroperoxide, or a ketone with hydroxyl group, hydroperoxy group, or oxo group introduced into carbon atom constituting the ring is obtained in a good yield; or a corresponding dicarboxylic acid where the ring has been oxidatively cleaved may be obtained in a good yield under some reaction conditions.

A reaction product obtained by using the catalyst may contain impurities derived from the catalyst or a denatured derivative (deactivated derivative) of the catalyst, and the quality of product may therefore be degraded. In particular, when a compound as a material for a polyester or polyimide, such as terephthalic acid or pyromellitic acid, contains such catalyst-derived impurities, there may occur disadvantages such as inhibition or polymerization reaction and coloring of a produced polymer, because the impurities generally contain nitrogen atom.

Patent Document 1: Japanese Unexamined Patent Application Publication (JP-A) No. 08-38909
Patent Document 2: Japanese Unexamined Patent Application Publication (JP-A) No. 09-327626
Patent Document 3: PCT International Publication Number WO 02/40154
Patent Document 4: Japanese Unexamined Patent Application Publication (JP-A) No. 2003-128618
Patent Document 5: PCT International Publication Number WO 03/28884
Patent Document 6: PCT International Publication Number WO 03/55600

DISCLOSURE OF INVENTION

Problems to be Solved by the Invention

Accordingly, an object of the present invention is to provide a method for easily removing catalyst-derived impurities from a reaction product obtained by the catalysis of a compound having a dicarboximide skeleton, to thereby yield a target compound with high purity efficiently.

Another object of the present invention is to provide a method for efficiently decomposing a compound having a dicarboximide skeleton.

Means for Solving the Problems

After intensive investigations to achieve the objects, the present inventors found that a compound having a dicarboximide skeleton can be easily decomposed into a low-molecular-weight compound or a compound highly soluble in water by treating the compound having a dicarboximide skeleton with hot water; and that, when a compound having a dicarboximide skeleton is used as a catalyst, impurities derived from the catalyst can be easily decomposed and removed from a reaction product by treating the reaction product with hot water. The present invention has been made based on these findings.

Specifically, according to the present invention, there is provided a method for producing an organic compound through a reaction of a substrate in the presence of a catalyst to yield a reaction product, in which the catalyst includes a compound having a dicarboximide skeleton represented by following Formula (i):

[Chemical Formula 1]

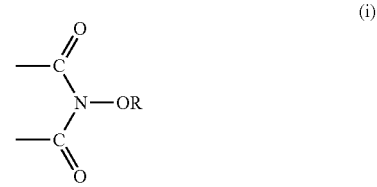

wherein R represents hydrogen atom or a hydroxyl-protecting group. The method includes the step of hydrothermally treating the reaction product with hot water so as to decompose and remove an impurity derived from the catalyst.

The compound having a dicarboximide skeleton includes, for example, a cyclic imide compound and a cyclic acylurea compound. The cyclic imide compound has a cyclic imide skeleton represented by following Formula (I):

[Chemical Formula 2]

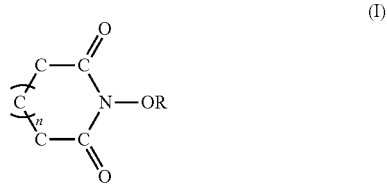

wherein "n" represents 0 or 1; and R represents hydrogen atom or a hydroxyl-protecting group, and the cyclic acylurea compound has a cyclic acylurea skeleton represented by following Formula (II):

[Chemical Formula 3]

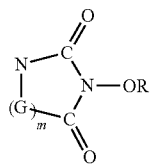
(II)

wherein "m" represents 1 or 2; G represents carbon atom or nitrogen atom, and, when "m" is 2, two Gs may be the same as or different from each other; and R is as defined above. The hydrothermal treatment in the production method is preferably carried out with hot water at 100° C. or higher.

According to another aspect of the present invention, there is provided a method for decomposing a compound having a dicarboximide skeleton. The method includes the step of hydrothermally treating a compound with hot water so as to decompose the compound, in which the compound has a dicarboximide skeleton represented by following Formula (i'):

[Chemical Formula 4]

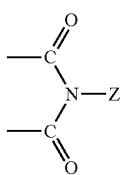
(i')

wherein Z represents hydrogen atom or an —OR group, wherein R represents hydrogen atom or a hydroxyl-protecting group.

The compound having a dicarboximide skeleton includes, for example, a cyclic imide compound and a cyclic acylurea compound, in which the cyclic imide compound has a cyclic imide skeleton represented by following Formula (I'):

[Chemical Formula 5]

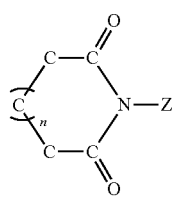
(I')

wherein "n" represents 0 or 1; Z represents hydrogen atom or an —OR group, wherein R represents hydrogen atom or a hydroxyl-protecting group, and the cyclic acylurea compound has a cyclic acylurea skeleton represented by following Formula (II'):

[Chemical Formula 6]

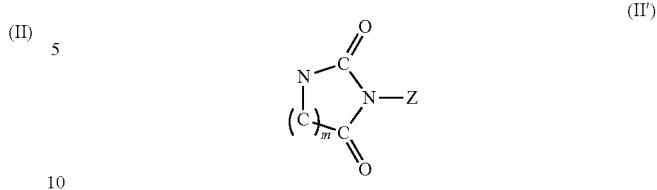
(II')

wherein "m" represents 1 or 2; G represents carbon atom or nitrogen atom, and, when "m" is 2, two Gs may be the same as or different from each other; and Z is as defined above. The hydrothermal treatment in the decomposition method is preferably carried out with hot water at 100° C. or higher.

ADVANTAGES

By a production method according to the present invention, a compound having a dicarboximide skeleton used as a catalyst and/or a denatured derivative thereof can be decomposed and removed through an easy or simple procedure, and a target compound with high purity can be efficiently produced. By a decomposition method according to the present invention, a compound having a dicarboximide skeleton can be decomposed through an easy or simple procedure.

BEST MODE FOR CARRYING OUT THE INVENTION

A method for producing an organic compound according to the present invention includes reacting a substrate in the presence of a catalyst including a compound having a dicarboximide skeleton represented by Formula (i). This method further includes the step of hydrothermally treating a reaction product with hot water so as to decompose and remove impurities derived from the catalyst. As a result of the hydrothermal treatment, the catalyst or a compound having a dicarboximide skeleton represented by Formula (i') as a denatured derivative of the catalyst can be decomposed into a low-molecular-weight compound and/or a compound having a high solubility in water. Thus, a target compound with high purity can be produced through a subsequent simple separation procedure. Of compounds each having a dicarboximide skeleton represented by Formula (i'), a compound wherein Z is an —OR group corresponds to a compound represented by Formula (i), i.e., the catalyst; and a compound wherein Z is hydrogen atom corresponds to one of denatured derivatives (deactivated derivatives) of the catalyst.

In Formula (i), R represents hydrogen atom or a hydroxyl-protecting group. When R is a hydroxyl-protecting group, two or more moieties corresponding to the skeleton represented by Formula (i), except R therefrom, may be combined through R.

A common hydroxyl-protecting group used in the field of organic synthesis can be used as the hydroxyl-protecting group represented by R. Examples of such protecting groups include alkyl groups (e.g., alkyl groups having one to four carbon atoms such as methyl and t-butyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); groups capable of forming an acetal or hemiacetal group with hydroxyl group, such as substituted methyl groups (e.g., methoxymethyl, methylthiomethyl, benzyloxymethyl, t-butoxymethyl, 2-methoxyethoxymethyl, 2,2,2-trichloroethoxymethyl, bis (2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, 2,2,2-trichloroethyl, and 2-methoxyethyl groups), tetrahydropyranyl group, tetrahydrofuranyl group, and 1-hydroxyalkyl groups (e.g., 1-hydroxyethyl, 1-hydroxyhexyl, 1-hydroxydecyl, 1-hydroxyhexadecyl, and 1-hydroxy-1-phenylmethyl groups); acyl groups (e.g., aliphatic saturated or unsaturated acyl groups including aliphatic acyl groups having one to twenty carbon atoms, such as formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, and stearoyl groups; acetoacetyl group; alicyclic acyl groups including cycloalkanecarbonyl groups such as cyclopentanecarbonyl and cyclohexanecarbonyl groups; and aromatic acyl groups such as benzoyl and naphthoyl groups), sulfonyl groups (e.g., methanesulfonyl, ethanesulfonyl, trifluoromethanesulfonyl, benzenesulfonyl, p-toluenesulfonyl, and naphthalenesulfonyl groups), alkoxycarbonyl groups (e.g., alkoxy-carbonyl groups whose alkoxy moiety has one to four carbon atoms, such as methoxycarbonyl, ethoxycarbonyl, and t-butoxycarbonyl groups), aralkyloxycarbonyl groups (e.g., benzyloxycarbonyl group and p-methoxybenzyloxycarbonyl group), substituted or unsubstituted carbamoyl groups (e.g., carbamoyl, methylcarbamoyl, and phenylcarbamoyl groups), groups corresponding to inorganic acids (e.g., sulfuric acid, nitric acid, phosphoric acid, and boric acid), except hydroxyl group (OH group) therefrom, dialkylphosphinothioyl groups (e.g., dimethylphosphinothioyl group), diarylphosphinothioyl groups (e.g., diphenylphosphinothioyl group), and substituted silyl groups (e.g., trimethylsilyl, t-butyldimethylsilyl, tribenzylsilyl, and triphenylsilyl group).

When two or more moieties corresponding to the skeleton represented by Formula (i), except R therefrom, are combined through R, examples of the R include polycarboxylic acyl groups such as oxalyl, malonyl, succinyl, glutaryl, adipoyl, phthaloyl, isophthaloyl, and terephthaloyl groups; carbonyl group; and polyvalent hydrocarbon groups such as methylene, ethylidene, isopropylidene, cyclopentylidene, cyclohexylidene, and benzylidene groups, of which groups capable of forming an acetal bond with two hydroxyl groups are preferred.

Preferred examples of R include hydrogen atom; groups capable of forming an acetal or hemiacetal group with hydroxyl group; and hydrolyzable protecting groups capable of leaving (deprotecting) through hydrolysis, including groups corresponding to acids, except hydroxyl group (OH group) therefrom, such as acyl groups, sulfonyl groups, alkoxycarbonyl groups, and carbamoyl groups. Examples of the acids include carboxylic acids, sulfonic acids, carbonic acids, carbamic acids, sulfuric acids, phosphoric acids, and boric acids.

Compounds having a dicarboximide skeleton represented by Formula (i) include cyclic imide compounds each having a cyclic imide skeleton represented by Formula (I). The cyclic imide compounds may each have two or more cyclic imide skeletons represented by Formula (I) per molecule. In the cyclic imide compounds, two or more moieties corresponding to the cyclic imide skeleton, except R, (N-oxy cyclic imide skeletons) may be combined through R.

In Formula (I), "n" represents 0 or 1. Specifically, Formula (I) represents a five-membered cyclic imide skeleton when "n" is 0, and it represents a six-membered cyclic imide skeleton when "n" is 1.

A representative example of the cyclic imide compound includes a compound represented by following Formula (1):

[Chemical Formula 7]

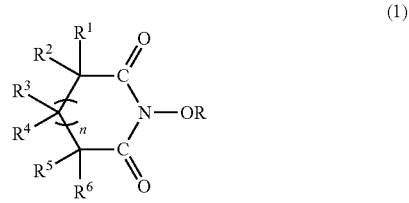

(1)

wherein "n" represents 0 or 1; R represents hydrogen atom or a hydroxyl-protecting group; $R^1$, $R^2$, $R^3$, $R^4$, $R^5$, and $R^6$ are the same as or different from one another and each represent hydrogen atom, a halogen atom, an alkyl group, an aryl group, a cycloalkyl group, hydroxyl group, an alkoxy group, carboxyl group, a substituted oxycarbonyl group, an acyl group, or an acyloxy group, wherein at least two of $R^1$, $R^2$, $R^3$, $R^4$, $R^5$, and $R^6$ may be combined to form a double bond, or an aromatic or non-aromatic ring, with carbon atom or carbon-carbon bond constituting the cyclic imide skeleton, and wherein the substituents $R^1$, $R^2$, $R^3$, $R^4$, $R^5$, and/or $R^6$, or the double bond or aromatic or non-aromatic ring formed by at least two of $R^1$, $R^2$, $R^3$, $R^4$, $R^5$, and $R^6$ may further have one or more cyclic imide groups represented by following Formula (a):

[Chemical Formula 8]

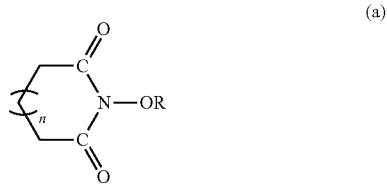

(a)

wherein "n" and R are as defined above.

Of the substituent $R^1$, $R^2$, $R^3$, $R^4$, $R^5$ and $R^6$ in these imide compounds represented by Formula (1), the halogen atoms include iodine, bromine, chlorine, and fluorine atoms. Examples of the alkyl groups include straight- or branched-chain alkyl groups having about one to about thirty carbon atoms, such as methyl, ethyl, propyl, isopropyl, butyl, isobutyl, s-butyl, t-butyl, hexyl, decyl, dodecyl, tetradecyl, and hexadecyl group, of which those having about one to about twenty carbon atoms are preferred.

The aryl groups include phenyl, tolyl, xylyl, and naphthyl groups and the like; and the cycloalkyl groups include cyclopentyl and cyclohexyl groups and the like. Examples of the alkoxy groups include alkoxy groups having about one to about thirty carbon atoms, such as methoxy, ethoxy, isopropoxy, butoxy, t-butoxy, hexyloxy, octyloxy, decyloxy, dodecyloxy, tetradecyloxy, and octadecyloxy groups, of which those having about one to about twenty carbon atoms are preferred.

Examples of the substituted oxycarbonyl groups include alkoxy-carbonyl groups whose alkoxy moiety has one to thirty carbon atoms, such as methoxycarbonyl, ethoxycarbonyl, isopropoxycarbonyl, butoxycarbonyl, t-butoxycarbonyl, hexyloxycarbonyl, decyloxycarbonyl, and hexadecyloxycarbonyl groups, of which alkoxy-carbonyl groups whose alkoxy moiety has one to twenty carbon atoms are preferred; cycloalkyloxycarbonyl groups such as cyclopentyloxycarbonyl and cyclohexyloxycarbonyl groups, of which cycloalkyloxycarbonyl groups having three to twenty members are preferred; aryloxycarbonyl groups such as phenyloxycarbonyl and naphthyloxycarbonyl groups, of which aryloxy-carbonyl groups whose aryloxy moiety has six to twenty carbon atoms are preferred; aralkyloxycarbonyl groups such as benzyloxycarbonyl group, of which aralkyloxy-carbonyl groups whose aralkyloxy moiety has seven to twenty-one carbon atoms are preferred.

Examples of the acyl groups include aliphatic saturated or unsaturated acyl group, including aliphatic acyl groups having one to thirty carbon atoms, such as formyl, acetyl, propionyl, butyryl, isobutyryl, valeryl, pivaloyl, hexanoyl, octanoyl, decanoyl, lauroyl, myristoyl, palmitoyl, and stearoyl groups, of which aliphatic acyl groups having one to twenty carbon atoms are preferred; acetoacetyl groups; alicyclic acyl groups including cycloalkanecarbonyl groups, etc., such as cyclopentanecarbonyl and cyclohexanecarbonyl groups; and aromatic acyl groups such as benzoyl and naphthoyl groups.

Examples of the acyloxy groups include aliphatic saturated or unsaturated acyloxy groups including aliphatic acyloxy groups having one to thirty carbon atoms, such as formyloxy, acetyloxy, propionyloxy, butyryloxy, isobutyryloxy, valeryloxy, pivaloyloxy, hexanoyloxy, octanoyloxy, decanoyloxy, lauroyloxy, myristoyloxy, palmitoyloxy, and stearoyloxy groups, of which aliphatic acyloxy groups having one to twenty carbon atoms are preferred; acetoacetyloxy group; alicyclic acyloxy groups including cycloalkanecarbonyloxy groups such as cyclopentanecarbonyloxy and cyclohexanecarbonyloxy groups; and aromatic acyloxy groups such as benzoyloxy and naphthoyloxy groups.

The substituents $R^1$, $R^2$, $R^3$, $R^4$, $R^5$, and $R^6$ may be the same as or different from one another. In Formula (1), at least two of $R^1$, $R^2$, $R^3$, $R^4$, $R^5$, and $R^6$ may be combined to form a double bond, or an aromatic or non-aromatic ring, with carbon atom or carbon-carbon bond constituting the cyclic imide skeleton. The aromatic or non-aromatic ring is preferably a ring having about five to about twelve members and is more preferably a ring having about six to about ten members. The aromatic or non-aromatic ring may be a heterocyclic ring or a fused heterocyclic ring; however, it is often a hydrocarbon ring. Examples of the ring include non-aromatic alicyclic rings including substituted or unsubstituted cycloalkane rings such as cyclohexane ring, and substituted or unsubstituted cycloalkene rings such as cyclohexene ring; non-aromatic bridged rings including substituted or unsubstituted bridged hydrocarbon rings such as 5-norbornene ring; and substituted or unsubstituted aromatic rings (including fused rings) such as benzene ring and naphthalene ring. The ring is often composed of an aromatic ring. The ring may have one or more substituents such as alkyl groups, haloalkyl groups, hydroxyl group, alkoxy groups, carboxyl group, substituted oxycarbonyl groups, acyl groups, acyloxy groups, nitro group, cyano group, amino groups, and halogen atoms.

The substituents $R^1$, $R^2$, $R^3$, $R^4$, $R^5$, and/or $R^6$, or the double bond or aromatic or non-aromatic ring formed by at least two of $R^1$, $R^2$, $R^3$, $R^4$, $R^5$ and $R^6$ may further have one or more cyclic imide groups represented by Formula (a). When $R^1$, $R^2$, $R^3$, $R^4$, $R^5$ or $R^6$ is, for example, an alkyl group having two or more carbon atoms, the cyclic imide group may be formed as including adjacent two carbon atoms constituting the alkyl group. When at least two of $R^1$, $R^2$, $R^3$, $R^4$, $R^5$, and $R^6$ are combined to form a double bond with carbon-carbon bond constituting the cyclic imide skeleton, the cyclic imide group may be formed as including the double bond. When at least two of $R^1$, $R^2$, $R^3$, $R^4$, $R^5$, and $R^6$ are combined to form an aromatic or non-aromatic ring together with carbon atom or carbon-carbon bond constituting the cyclic imide skeleton, the cyclic imide group may be formed as including adjacent two carbon atoms constituting the ring.

Preferred imide compounds include compounds represented by following formulae:

[Chemical Formula 9]

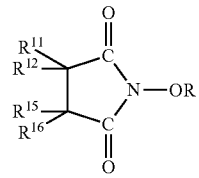
(1a)

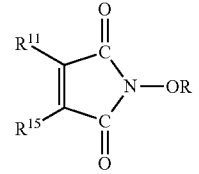
(1b)

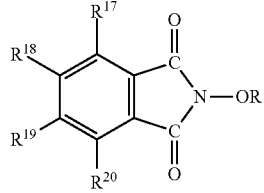
(1c)

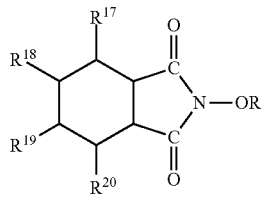
(1d)

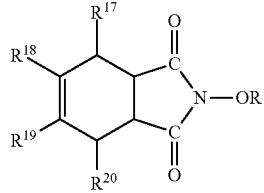
(1e)

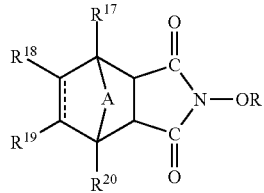
(1f)

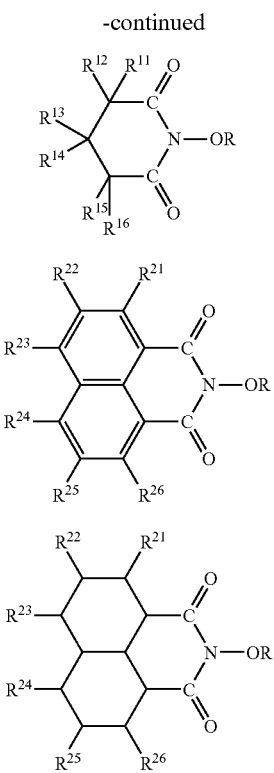

wherein $R^{11}$, $R^{12}$, $R^{13}$ $R^{14}$, $R^{15}$, and $R^{16}$ are the same as or different from one another and each represent hydrogen atom, a halogen atom, an alkyl group, an aryl group, a cycloalkyl group, hydroxyl group, an alkoxy group, carboxyl group, a substituted oxycarbonyl group, an acyl group, or an acyloxy group; $R^{17}$, $R^{18}$, $R^{19}$, $R^{20}$, $R^{21}$, $R^{22}$, $R^{23}$, $R^{24}$, $R^{25}$, and $R^{26}$ are the same as or different from one another and each represent hydrogen atom, an alkyl group, a haloalkyl group, hydroxyl group, an alkoxy group, carboxyl group, a substituted oxycarbonyl group, an acyl group, an acyloxy group, nitro group, cyano group, an amino group, or a halogen atom, wherein adjacent groups of $R^{17}$ to $R^{26}$ may be combined to form a five-membered or six-membered cyclic imide skeleton indicated in Formula (1c), (1d), (1e), (1f), (1h) or (1i), and wherein "A" in Formula (1f) represents methylene group or oxygen atom; and R is as defined above.

Examples of the halogen atoms, alkyl groups, aryl groups, cycloalkyl groups, hydroxyl group, alkoxy groups, carboxyl group, substituted oxycarbonyl groups, acyl groups, and acyloxy groups in the substituents $R^{11}$ to $R^{16}$ are as with the corresponding groups in $R^1$ to $R^6$ In the substituents $R^{17}$ to $R^{26}$, examples of the alkyl groups are as with the above-exemplified alkyl groups, of which alkyl groups having about one to about six carbon atoms are preferred. The haloalkyl groups include haloalkyl groups having about one to about four carbon atoms, such as trifluoromethyl group. Examples of the alkoxy groups are as with those mentioned above, of which lower alkoxy groups having about one to about four carbon atoms are preferred. Examples of the substituted oxycarbonyl groups are as with those mentioned above, such as alkoxycarbonyl groups, cycloalkyloxycarbonyl groups, aryloxycarbonyl groups, and aralkyloxycarbonyl groups. Examples of the acyl groups are as with those mentioned above, such as aliphatic saturated or unsaturated acyl groups, acetoacetyl group, alicyclic acyl groups, and aromatic acyl groups. Examples of the acyloxy groups are as with those mentioned above, such as aliphatic saturated or unsaturated acyloxy groups, acetoacetyloxy group, alicyclic acyloxy groups, and aromatic acyloxy groups. Examples of the halogen atoms include fluorine, chlorine, and bromine atoms. Each of the substituents $R^{17}$ to $R^{26}$ is generally frequently one of hydrogen atom, a lower alkyl group having about one to about four carbon atoms, carboxyl group, a substituted oxycarbonyl group, nitro group, and a halogen atom.

Of preferred imide compounds, representative examples of compounds each having a five-membered N-substituted cyclic imide skeleton include compounds of Formula (1) wherein R is hydrogen atom, such as N-hydroxysuccinimide, N-hydroxy-α-methylsuccinimide, N-hydroxy-α,α-dimethylsuccinimide, N-hydroxy-α,β-dimethylsuccinimide, N-hydroxy-α,α,β,β-tetramethylsuccinimide, N-hydroxymaleimide, N-hydroxyhexahydrophthalimide, N,N'-dihydroxycyclohexanetetracarboxylic diamide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitic diimide, N,N'-dihydroxynaphthalenetetracarboxylic diimide, α,β-diacetoxy-N-hydroxysuccinimide, N-hydroxy-α,β-bis(propionyloxy)succinimide, N-hydroxy-α,β-bis(valeryloxy)succinimide, N-hydroxy-α,β-bis(lauroyloxy)succinimide, α,β-bis(benzoyloxy)-N-hydroxysuccinimide, N-hydroxy-4-methoxycarbonylphthalimide, 4-chloro-N-hydroxyphthalimide, 4-ethoxycarbonyl-N-hydroxyphthalimide, N-hydroxy-4-pentyloxycarbonylphthalimide, 4-dodecyloxy-N-hydroxycarbonylphthalimide, N-hydroxy-4-phenoxycarbonylphthalimide, N-hydroxy-4,5-bis(methoxycarbonyl)phthalimide, 4,5-bis(ethoxycarbonyl)-N-hydroxyphthalimide, N-hydroxy-4,5-bis(pentyloxycarbonyl)phthalimide, 4,5-bis(dodecyloxycarbonyl)-N-hydroxyphthalimide, and N-hydroxy-4,5-bis(phenoxycarbonyl)phthalimide; compounds corresponding to these compounds, except with R being an acyl group such as acetyl group, propionyl group, or benzoyl group; compounds of Formula (1), wherein R is a group capable of forming an acetal or hemiacetal bond with hydroxyl group, such as N-methoxymethyloxyphthalimide, N-(2-methoxyethoxymethyloxy)phthalimide, and N-tetrahydropyranyloxyphthalimide; compounds of Formula (1) wherein R is a sulfonyl group, such as N-methanesulfonyloxyphthalimide and N-(p-toluenesulfonyloxy)phthalimide; and compounds of Formula (1) wherein R is a group corresponding to an inorganic acid, except hydroxyl group (OH group) therefrom, such as sulfuric acid ester, nitric acid ester, phosphoric acid ester, or boric acid ester of N-hydroxyphthalimide.

Of preferred imide compounds, representative examples of compounds each having a six-membered N-substituted cyclic imide skeleton include compounds of Formula (1) wherein R is hydrogen atom, such as N-hydroxyglutarimide, N-hydroxy-α,α-dimethylglutarimide, N-hydroxy-β,β-dimethylglutarimide, N-hydroxy-1,8-decalindicarboximide, N,N'-dihydroxy-1,8; 4,5-decalintetracarboxylic diimide, N-hydroxy-1,8-naphthalenedicarboximide(N-hydroxynaphthalimide), and N,N'-dihydroxy-1,8; 4,5-naphthalenetetracarboxylic diimide; compounds corresponding to these compounds, except with R being an acyl group such as acetyl group, propionyl group, or benzoyl group; compounds of Formula (1) wherein R is a group capable of forming an acetal or hemiacetal bond with hydroxyl group, such as N-methoxymethyloxy-1,8-naphthalenedicarboximide and N,N'-bis(methoxymethyloxy)-1,8; 4,5-naphthalenetetracarboxylic diimide; compounds of Formula (1) wherein R is a sulfonyl group, such as N-methanesulfonyloxy-1,8-naphthalenedicarboximide and N,N'-bis(methanesulfonyloxy)-1,8; 4,5-naphthalenetetracarboxylic diimide; and compounds of Formula (1) wherein R is a group corresponding to an inorganic acid, except hydroxyl group (OH group) therefrom, such as sulfuric acid ester, nitric acid ester, phosphoric acid ester, and boric acid ester of N-hydroxy-1,8-naphthalenedicarboximide and N,N'-dihydroxy-1,8; 4,5-naphthalenetetracarboxylic diimide, respectively.

The compounds each having a dicarboximide skeleton represented by Formula (i) include, in addition to the cyclic imide compounds, cyclic acylurea compounds each having a cyclic acylurea skeleton [—C(=O)—N—C(=O)—N-] represented by Formula (II). The cyclic acylurea compounds may each have two or more cyclic acylurea skeletons represented by Formula (II) per molecule. These cyclic acylurea compounds may each have two or more moieties (N-oxy cyclic acylurea skeletons) corresponding to the cyclic acylurea skeleton represented by Formula (II), except R therefrom, which are combined through R. The atom G constituting the cyclic acylurea skeleton, and nitrogen atom bonded to G may each have one or more different substituents. A non-aromatic or aromatic ring may be fused to the cyclic acylurea skeleton, and the cyclic acylurea skeleton may have a double bond on its ring.

Such cyclic acylurea skeletons represented by Formula (II) include 3-hydroxy (or 3-substituted oxy)-hydantoin skeletons represented by following Formula (IIa); 4-hydroxy (or 4-substituted oxy)-1,2,4-triazolidine-3,5-dione skeletons [including 4-hydroxy (or 4-substituted oxy)-1,2,4-triazoline-3,5-dione skeletons] represented by Formula (IIb); hydro-3-hydroxy (or 3-substituted oxy)-1,3-diazine-2,4-dione skeletons [including hexahydro-1-hydroxy (or 1-substituted oxy)-1,3-diazine-2,4,6-trione skeletons, hexahydro-1,3-dihydroxy (or 1,3-bis-substituted oxy)-1,3-diazine-2,4,6-trione skeletons, and 3-hydroxy (or 3-substituted oxy)uracil skeletons] represented by Formula (IIc); hydro-4-hydroxy (or 4-substituted oxy)-1,2,4-triazine-3,5-dione skeletons represented by Formula (IId); hydro-1-hydroxy (or 1-substituted oxy)-1,3,5-triazine-2,6-dione skeletons represented by Formula (IIe); and hydro-5-hydroxy (or 5-substituted oxy)-1,2,3,5-tetrazine-4,6-dione skeletons represented by Formula (IIf):

[Chemical Formula 10]

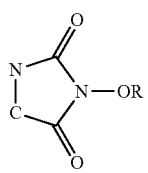

(IIa)

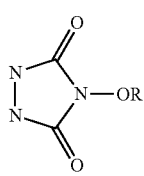

(IIb)

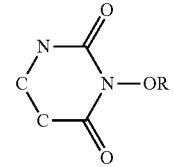

(IIc)

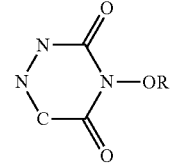

(IId)

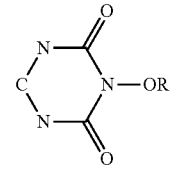

(IIe)

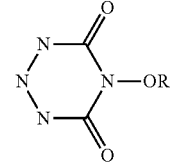

(IIf)

wherein R is as defined above.

Representative examples of the cyclic acylurea compounds include hydro-1-hydroxy (or 1-substituted oxy)-1,3,5-triazine-2,6-dione compounds represented by following Formula (2):

[Chemical Formula 11]

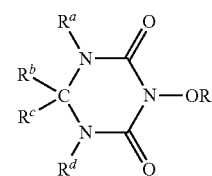

(2)

wherein $R^a$ and $R^d$ are the same as or different from one another and each represent hydrogen atom, an alkyl group, an aryl group, a cycloalkyl group, a protected or unprotected hydroxyl group, a protected or unprotected carboxyl group, or an acyl group; $R^b$ and $R^c$ are the same as or different from one another and each represent hydrogen atom, a halogen atom, an alkyl group, an aryl group, a cycloalkyl group, hydroxyl group, an alkoxy group, carboxyl group, a substituted oxycarbonyl group, an acyl group, or an acyloxy group, wherein at least two of $R^a$, $R^b$, $R^c$ and $R^d$ may be combined to form a double bond or an aromatic or non-aromatic ring together with an atom constituting the ring in Formula (2), and $R^b$ may $R^c$ together form oxo group; and R is as defined above.

In Formula (2), examples of the alkyl groups, aryl groups, cycloalkyl groups, and acyl groups as $R^a$ and $R^d$ are as with the corresponding alkyl groups and other groups in $R^1$ to $R^6$; and the hydroxyl-protecting groups are as with those mentioned above.

Examples of the carboxyl-protecting groups include protecting groups commonly used in the field of organic synthesis, including alkoxy groups including alkoxy groups having one to six carbon atoms, such as methoxy, ethoxy, and butoxy; cycloalkyloxy groups; aryloxy groups such as phenoxy group; aralkyloxy groups such as benzyloxy group; trialkylsilyloxy groups such as trimethylsilyloxy group; and substituted or unsubstituted amino groups including amino group and mono- or di-alkylamino groups whose alkyl moiety has one to six carbon atoms, such as methylamino group and dimethylamino group.

Examples of the halogen atoms, alkyl groups, aryl groups, cycloalkyl groups, hydroxyl groups, alkoxy groups, carboxyl groups, substituted oxycarbonyl groups, acyl groups, and acyloxy groups as $R^b$ and $R^c$ are as with the alkyl groups and other groups in $R^1$ to $R^6$.

In Formula (2), at least two of $R^a$, $R^b$, $R^c$ and $R^d$ may be combined to form a double bond or an aromatic or non-aromatic ring together with an atom (carbon atom and/or nitrogen atom) constituting the ring in Formula (2), and $R^b$ and $R^c$ may together form oxo group. Preferred examples of the aromatic or non-aromatic ring are as exemplified above.

Of compounds represented by Formula (2), preferred are isocyanuric acid derivatives represented by following Formula (2a):

[Chemical Formula 12]

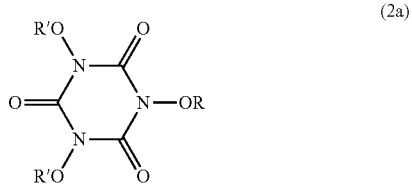

(2a)

wherein R, R', and R" are the same as or different from one another and each represent hydrogen atom or a hydroxyl-protecting group.

Representative examples of the cyclic acylurea compounds include compounds each having a skeleton represented by Formula (IIa), such as 3-hydroxyhydantoin, 1,3-dihydroxyhydantoin, 3-hydroxy-1-methylhydantoin, 3-acetoxyhydantoin, 1,3-diacetoxyhydantoin, and 3-acetoxy-1-methylhydantoin; compounds each having a skeleton represented by Formula (IIb), such as 4-hydroxy-1,2,4-triazolidine-3,5-dione, 4-hydroxy-1,2-dimethyl-1,2,4-triazolidine-3,5-dione, 4-acetoxy-1,2,4-triazolidine-3,5-dione, 4-acetoxy-1,2-dimethyl-1,2,4-triazolidine-3,5-dione, 4-hydroxy-1,2,4-triazoline-3,5-dione, and 4-acetoxy-1,2,4-triazoline-3,5-dione; compounds each having a skeleton represented by Formula (IIc), such as hexahydro-3-hydroxy-1,3-diazine-2,4-dione, hexahydro-1,3-dihydroxy-1,3-diazine-2,4-dione, hexahydro-3-hydroxy-1-methyl-1,3-diazine-2,4-dione, 3-acetoxy-hexahydro-1,3-diazine-2,4-dione, 1,3-diacetoxy-hexahydro-1,3-diazine-2,4-dione, 3-acetoxy-hexahydro-1-methyl-1,3-diazine-2,4-dione, hexahydro-1-hydroxy-1,3-diazine-2,4,6-trione, 1-acetoxy-hexahydro-1,3-diazine-2,4,6-trione, hexahydro-1,3-dihydroxy-1,3-diazine-2,4,6-trione, 1,3-diacetoxy-hexahydro-1,3-diazine-2,4,6-trione, 3-hydroxyuracil, and 3-acetoxyuracil; compounds each having a skeleton represented by Formula (IId), such as hexahydro-4-hydroxy-1,2,4-triazine-3,5-dione, hexahydro-4-hydroxy-1,2-dimethyl-1,2,4-triazine-3,5-dione, 4-acetoxy-hexahydro-1,2,4-triazine-3,5-dione, and 4-acetoxy-hexahydro-1,2-dimethyl-1,2,4-triazine-3,5-dione; compounds each having a skeleton represented by Formula (IIe) [e.g., compounds represented by Formula (2)], such as hexahydro-1,3,5-trihydroxy-1,3,5-triazine-2,4,6-trione (i.e., 1,3,5-trihydroxyisocyanuric acid), 1,3,5-triacetoxy-hexahydro-1,3,5-triazine-2,4,6-trione, 1,3,5-tris(benzoyloxy)-hexahydro-1,3,5-triazine-2,4,6-trione, hexahydro-1,3,5-tris(methoxymethyloxy)-1,3,5-triazine-2,4,6-trione, hexahydro-1-hydroxy-1,3,5-triazine-2,6-dione, hexahydro-1-hydroxy-3,5-dimethyl-1,3,5-triazine-2,6-dione, 1-acetoxy-hexahydro-1,3,5-triazine-2,6-dione, and 1-acetoxy-hexahydro-3,5-dimethyl-1,3,5-triazine-2,6-dione; and compounds each having a skeleton represented by Formula (I-f), such as hexahydro-5-hydroxy-1,2,3,5-tetrazine-4,6-dione, hexahydro-5-hydroxy-1,2,3-trimethyl-1,2,3,5-tetrazine-4,6-dione, 5-acetoxy-hexahydro-1,2,3,5-tetrazine-4,6-dione, and 5-acetoxy-hexahydro-1,2,3-trimethyl-1,2,3,5-tetrazine-4,6-dione.

Of the compounds each having a dicarboximide skeleton, a compound wherein R is hydrogen atom (N-hydroxy cyclic compound) can be prepared according to a known process or a combination of known processes. Of the compounds each having a dicarboximide skeleton, a compound wherein R is a hydroxyl-protecting group can be prepared by introducing a desired protecting group into a corresponding compound wherein R is hydrogen atom (N-hydroxy cyclic compound) using a common reaction for introducing a protecting group.

More specifically, of the cyclic imide compounds, a compound wherein R is hydrogen atom (N-hydroxy cyclic imide compound) can be prepared by a common process using an imidation reaction (a reaction for the formation of an imide), such as a process of allowing a corresponding acid anhydride to react with hydroxylamine to perform ring-opening of an acid anhydride group, and closing the ring thereof to yield an imide. N-acetoxyphthalimide, for example, can be prepared by allowing N-hydroxyphthalimide to react with acetic anhydride or allowing N-hydroxyphthalimide to react with an acetyl halide in the presence of a base. The compound can also be prepared by another process.

Examples of typically preferred cyclic imide compounds as the catalyst include N-hydroxyamide compounds each derived from an aliphatic polycarboxylic anhydride (cyclic anhydride) or an aromatic polycarboxylic anhydride (cyclic anhydride), such as N-hydroxysuccinimide, N-hydroxyphthalimide, N,N'-dihydroxypyromellitic diimide, N-hydroxyglutarimide, N-hydroxy-1,8-naphthalenedicarboximide, and N,N'-dihydroxy-1,8; 4,5-naphthalenetetracarboxylic diimide; and compounds corresponding to the N-hydroxyamide compounds, obtained by introducing a protecting group into the hydroxyl group thereof.

Of the cyclic acylurea compounds, for example, 1,3,5-triacetoxy-hexahydro-1,3,5-triazine-2,4,6-trione (i.e., 1,3,5-triacetoxyisocyanuric acid) is available by allowing hexahydro-1,3,5-trihydroxy-1,3,5-triazine-2,4,6-trione (i.e., 1,3,5-trihydroxyisocyanuric acid) to react with acetic anhydride or allowing this compound to react with an acetyl halide in the presence of a base.

Each of compounds having a dicarboximide skeleton represented by Formula (i) can be used alone or in combination in reactions. For example, a cyclic imide compound having a cyclic imide skeleton represented by Formula (I) can be used in combination typically with a cyclic acylurea compound having a cyclic acylurea skeleton represented by Formula (II). A catalyst including a compound having a dicarboximide skeleton can be formed within the reaction system. A catalyst including a compound having a dicarboximide skeleton can be used as a catalyst supported on a support. The support used herein is often a porous support such as activated carbon, zeolite, silica, silica-alumina, or bentonite. The amount of the compound having a dicarboximide skeleton on a support is, for example, about 0.1 to about 50 parts by weight, preferably about 0.5 to about 30 parts by weight, and more preferably about 1 to about 20 parts by weight, to 100 parts by weight of the support.

The amount of a catalyst including a compound having a dicarboximide skeleton can be selected within a wide range and is, for example, about 0.0000001 to about 1 mole, preferably about 0.000001 to about 0.5 mole, and more preferably about 0.00001 to about 0.4 mole, to 1 mole of the reaction component (substrate).

A promoter (co-catalyst) can be used in combination with the catalyst including a compound having a dicarboximide skeleton in the present invention. Examples of the promoter include metal compounds. The combination use of the nitrogen-containing cyclic compound catalyst with a metal compound can improve the rate and selectivity of a reaction.

A metallic element constituting the metal compound is not specifically limited but is often a metallic element belonging to Groups 1 to 15 of the Periodic Table of Elements. The term "metallic element" as used herein also includes boron B. Preferred metallic elements include transition metal elements (elements belonging to Groups 3 to 12 of the Periodic Table of Elements). Among them, for example, Mn, Co, Zr, Ce, Fe, V, and Mo are more preferred, of which Mn and Co are particularly preferred. The activity may increase through the combination use of a transition metal element with an element belonging to Group 1 or 2 of the Periodic Table of Elements. These metal elements may each have any valence not specifically limited and may have, for example, a valence of about zero to about six.

Examples of such metallic compounds include inorganic compounds of the metallic elements, including elementary substances, hydroxides, oxides (including multiple oxides), halides (fluorides, chlorides, bromides, and iodides), salts of oxoacids (e.g., nitrates, sulfates, phosphates, borates, and carbonates), salts of isopolyacids, and salts of heteropolyacids; and organic compounds of the metallic elements, including salts of organic acids (e.g., acetates, propionates, prussiates, naphthenates, and stearates) and complexes. Ligands for constituting the complexes include OH (hydroxo), alkoxys (e.g., methoxy, ethoxy, propoxy, and butoxy), acyls (e.g., acetyl and propionyl), alkoxycarbonyls (e.g., methoxycarbonyl and ethoxycarbonyl), acetylacetonato, cyclopentadienyl group, halogen atoms (e.g., chlorine and bromine), CO, CN, oxygen atom, $H_2O$ (aquo), phosphorus compounds including phosphines (e.g., triarylphosphines such as triphenylphohsphine), and nitrogen-containing compounds such as $NH_3$ (amine), NO, $NO_2$ (nitro), $NO_3$ (nitrato), ethylenediamine, diethylenetriamine, pyridine, and phenanthroline.

Specific examples of the metallic compounds include, by taking cobalt compounds as an example, divalent or trivalent cobalt compounds including inorganic compounds such as cobalt hydroxide, cobalt oxide, cobalt chloride, cobalt bromide, cobalt nitrate, cobalt sulfate, and cobalt phosphate; salts of organic acids, such as cobalt acetate, cobalt naphthenate, and cobalt stearate; and complexes such as cobalt acetylacetonate. Illustrative vanadium compounds include divalent, trivalent, tetravalent, or pentavalent vanadium compounds including inorganic compounds such as vanadium hydroxide, vanadium oxide, vanadium chloride, vanadyl chloride, vanadium sulfate, vanadyl sulfate, and sodium vanadate; and complexes such as vanadium acetylacetonate and vanadyl acetylacetonate. Examples of sodium compounds as compounds of an element belonging to Group 1 of the Periodic Table of Elements include inorganic compounds (including elementary sodium) such as sodium, sodium hydroxide, sodium carbonate, sodium hydrogen carbonate, sodium chloride, and sodium sulfate; and organic compounds such as sodium methoxide, sodium ethoxide, sodium acetate, sodium benzoate, and sodium p-toluenesulfonate. Examples of compounds of the other metal elements includes compounds corresponding to the cobalt compounds, vanadium compounds, or sodium compounds. Each of the metal compounds can be used alone or in combination. In particular, the combination use of a cobalt compound and a manganese compound, and, where necessary, a zirconium compound may often remarkably increase the reaction rate. The combination use of two or more metal compounds each having different valences (e.g., a divalent metal compound and a trivalent metal compound) is also desirable. A catalyst including a compound of Formula (I) or (II) wherein X is an —OR group and R is a hydroxyl-protecting group is desirably used in combination with a transition metal element compound, such as a cobalt compound, and a compound of an element belonging to Group 1 or Group 2 of the Periodic Table of Elements as metal compounds. In this case, a high catalytic activity can be provided and a reaction between the substrate and the catalyst can be suppressed even in a reaction in a non-acidic solvent or an aprotic solvent.

The amount of the metal compound(s) is, for example, about 0.0001 to about 10 moles and preferably about 0.005 to about 3 moles, to 1 mole of the catalyst including a compound having a dicarboximide skeleton. The amount of the metal compound(s) is, for example, about 0.00001 percent by mole to about 10 percent by mole, preferably about 0.1 percent by mole to about 5 percent by mole, to the reaction component (substrate).

The promoters for use in the present invention also include organic salts each comprising a polyatomic cation or a polyatomic anion and its counter ion, which polyatomic cation or anion contains an element belonging to Group 15 or Group 16 of the Periodic Table of Elements having at least one organic group bonded therewith. By using the organic salts as the promoters, the rate and selectivity of the reaction can further be improved. In the organic salts, the Group 15 elements of the Periodic Table of Elements include N, P, As, Sb, and Bi, and the Group 16 elements of the Periodic Table of Elements include, for example, O, S, Se, and Te. Preferred elements are N, P, As, Sb, and S, of which N, P, and S are typically preferred. Representative examples of the organic salts include organic onium salts including organic ammonium salts such as tetrabutylammonium chloride; organic phosphonium salts such as tetrabutylphosphonium chloride; and organic sulfonium salts such as triethylsulfonium iodide. The amount of the organic salt(s) is, for example, about 0.001 to about 0.1 mole, and preferably about 0.005 to about 0.08 mole, to 1 mole of the catalyst including a compound having a dicarboximide skeleton.

The promoters for use in the present invention further include strong acids such as compounds having a pKa of 2 (25° C.) or less. Preferred examples of the strong acids include hydrogen halides, halogen acids, sulfuric acid, and heteropolyacids. The amount of strong acid(s) is, for example, about 0.001 to about 3 moles to 1 mole of the catalyst including a compound having a dicarboximide skeleton.

The promoters for use in the present invention also include compounds each having a carbonyl group bonded with an electron attracting group. Representative examples of such compounds each having a carbonyl group bonded with an electron attracting group include hexafluoroacetone, trifluoroacetic acid, pentafluorophenyl ketone, and benzoic acid.

The amount of the compound(s) is, for example, from about 0.0001 to about 3 moles to 1 mole (on the basis of charged amount) of the reaction component (substrate).

The reaction system may further contain a free-radical generator or a free-radical reaction accelerator. Examples of such components include halogens such as chlorine and bromine; peracids such as peracetic acid and m-chloroperbenzoic acid; peroxides including hydroperoxides such as hydrogen peroxide and t-butyl hydroperoxide (TBHP); nitric acid, nitrous acid, and salts of them; nitrogen dioxide; and aldehydes such as benzaldehyde. When the target compound is an aromatic carboxylic acid or an aromatic carboxylic anhydride, the aldehyde herein may for example be an aldehyde corresponding to the target compound. The existence of the component in the system may enhance a reaction. The amount of the above-mentioned component is, for example, from about 0.001 to about 3 mole to 1 mole of the catalyst including a compound having a dicarboximide skeleton.

Reactions in the present invention include all reactions in which the compound having a dicarboximide skeleton exhibits a catalytic activity. Details of these reactions can be found, for example, in above-mentioned Japanese Unexamined Patent Application Publication (JP-A) No. 08-38909, JP-A No. 09-327626, PCT International Publication Number WO 02/40154, JP-A No. 2003-128618, PCT International Publication Number WO 03/28884, and PCT International Publication Number WO 03/55600. A representative reaction of the reactions in which the compound having a dicarboximide skeleton exhibits a catalytic activity is a reaction between a radical-formable compound (A) and a radical-scavenging compound (B). The reaction between a radical-formable compound (A) and a radical-scavenging compound (B) can yield an addition or substitution reaction product between the compound (A) and the compound (B) or a derivative thereof. Examples of such derivatives include an oxidation reaction product, a cyclization reaction product, a dehydration reaction product, a decarboxylation reaction product, a rearrangement reaction product, and an isomerization reaction product.

[Radical-Formable Compound (A)]

The radical-formable compound (A) is not specifically limited, as long as it can form a stable free radical; and representative examples thereof include (A1) heteroatom-containing compounds each having a carbon-hydrogen bond at the adjacent position to the heteroatom, (A2) compounds each having a carbon-heteroatom double bond, (A3) compounds each having a methine carbon atom, (A4) compounds each having a carbon-hydrogen bond at the adjacent position to an unsaturated bond, (A5) non-aromatic cyclic hydrocarbons, (A6) conjugated compounds, (A7) amines, (A8) aromatic compounds, (A9) straight-chain alkanes, and (A10) olefins. These compounds may each have one or more substituents, within ranges not adversely affecting the reaction. A radical-formable compound (A) functions as a radical-donating compound.

Examples of the heteroatom-containing compounds (A1) each having a carbon-hydrogen bond at the adjacent position to the heteroatom include (A1-1) primary or secondary alcohols and primary or secondary thiols, (A1-2) ethers each having a carbon-hydrogen bond at the adjacent position to oxygen atom, and sulfides each having a carbon-hydrogen bond at the adjacent position to sulfur atom, (A1-3) acetals (including hemiacetals) each having a carbon-hydrogen bond at the adjacent position to oxygen atom, and thioacetals (including thiohemiacetals) each having a carbon-hydrogen bond at the adjacent position to sulfur atom.

The primary or secondary alcohols as the compounds (A1-1) include a wide variety of alcohols. These alcohols may be whichever of monohydric, dihydric, and polyhydric alcohols. Representative examples of the primary alcohols include saturated or unsaturated aliphatic primary alcohols each having about one to about thirty carbon atoms, such as methanol, ethanol, 1-propanol, 1-butanol, 1-hexanol, ethylene glycol, and pentaerythritol, of which those having about one to about twenty carbon atoms are preferred, and those having about one to about fifteen carbon atoms are more preferred; saturated or unsaturated alicyclic primary alcohols such as cyclohexylmethyl alcohol; aromatic primary alcohols such as benzyl alcohol and cinnamyl alcohol; and heterocyclic alcohols such as 2-hydroxymethylpyridine. Representative examples of secondary alcohols include saturated or unsaturated aliphatic secondary alcohols having about three to about thirty carbon atoms, including 2-propanol, s-butyl alcohol, and vicinal diols such as 1,2-propanediol, of which those having about three to about twenty carbon atoms are preferred, and those having about three to about fifteen carbon atoms are more preferred; secondary alcohols each having an aliphatic hydrocarbon group and an alicyclic hydrocarbon group (e.g., a cycloalkyl group) bonded to a carbon atom that is bonded to a hydroxyl group, such as 1-cyclohexylethanol; saturated or unsaturated alicyclic secondary alcohols (inclusive of bridged secondary alcohols) each having about three to about twenty members, such as cyclohexanol, 2-adamantanol, 2-adamantanols each having one to four hydroxyl groups at the bridgehead positions, and 2-adamantanols each having an oxo group on the adamantane ring, of which those having about three to about fifteen members are preferred, those having about five to about fifteen members are more preferred, and those having about five to about eight members are particularly preferred; aromatic secondary alcohols such as 1-phenylethanol; and heterocyclic secondary alcohols such as 1-(2-pyridyl)ethanol. Representative examples of the alcohols further include alcohols each having a bridged hydrocarbon group, including compounds each having a bridged hydrocarbon group bonded to the carbon atom to which a hydroxyl group is bonded, such as 1-adamantanemethanol, α-methyl-2-tricyclo[$5.2.1.0^{2,6}$]decanemethanol, α-methyl-1-norbornanemethanol, and α-methyl-2-norbornene-1-methanol.

The primary or secondary thiols as the compounds (A1-1) include thiols corresponding to the above-mentioned primary or secondary alcohols.

The ethers each having a carbon-hydrogen bond at the adjacent position to oxygen atom as the compounds (A1-2) include, for example, aliphatic ethers such as dimethyl ether, diethyl ether, dipropyl ether, dibutyl ether, diallyl ether, and methyl vinyl ether; aromatic ethers such as anisole, dibenzyl ether, and phenyl benzyl ether; and cyclic ethers to which an aromatic ring or non-aromatic ring may be fused, such as dihydrofuran, tetrahydrofuran, pyran, dihydropyran, tetrahydropyran, morpholine, chroman, and isochroman.

The sulfides each having a carbon-hydrogen bond at the adjacent position to sulfur atom as the compounds (A1-2) include sulfides corresponding to the above-mentioned ethers each having a carbon-hydrogen bond at the adjacent position to oxygen atom.

The acetals each having a carbon-hydrogen bond at the adjacent position to oxygen atom as the compounds (A1-3) include, for example, acetals each derived from an aldehyde with an alcohol or an acid anhydride. Such acetals include cyclic acetals and acyclic acetals. Examples of the aldehyde include aliphatic aldehydes such as formaldehyde, acetaldehyde, propionaldehyde, butyraldehyde, isobutyraldehyde, hexanal, and decanal; alicyclic aldehydes such as cyclopentanecarbaldehyde and cyclohexanecarbaldehyde; and aromatic aldehydes such as benzaldehyde and phenylacetaldehyde. Examples of the alcohol include monohydric alcohols such as methanol, ethanol, 1-propanol, 1-butanol, and benzyl alcohol; and dihydric alcohols such as ethylene glycol, propylene glycol, and 1,3-propanediol. Representative examples of the acetals include 1,3-dioxolane compounds such as 1,3-dioxolane and 2-methyl-1,3-dioxolane; 1,3-dioxane compounds such as 2-methyl-1,3-dioxane; and dialkylacetal compounds such as acetaldehyde dimethyl acetal.

The sulfides each having a carbon-hydrogen bond at the adjacent position to sulfur atom as the compounds (A1-3) include sulfides corresponding to the above-mentioned ethers each having a carbon-hydrogen bond at the adjacent position to oxygen atom.

The compounds (A2) each having a carbon-heteroatom double bond include, for example, (A2-1) carbonyl-containing compound, (A2-2) thiocarbonyl-containing compound, and (A2-3) imines. The carbonyl-containing compounds (A2-1) include ketones and aldehydes. Examples thereof include chain ketones such as acetone, methyl ethyl ketone, methyl isobutyl ketone, methyl isopropenyl ketone, methyl cyclohexyl ketone, acetophenone, and methyl (2-pyridyl) ketone; cyclic ketones such as cyclopentanone, cyclohexanone, isophorone, cyclododecanone, and 2-adamantanone; 1,2-dicarbonyl compounds (e.g., α-diketones), such as biacetyl (2,3-butanedione), 2,3-pentanedione, and bibenzoyl (benzil); α-keto-alcohols such as acetoin and benzoin; aliphatic aldehydes such as acetaldehyde, propionaldehyde, butanal, hexanal, succinaldehyde, glutaraldehyde, and adipaldehyde; alicyclic aldehydes such as cyclohexyl aldehyde, citral, and citronellal; aromatic aldehydes such as benzaldehyde, carboxybenzaldehyde, cinnamaldehyde, salicylaldehyde, anisaldehyde, phthalaldehyde, isophthalaldehyde, and terephthalaldehyde; and heterocyclic aldehydes such as furfural and nicotinaldehyde.

The thiocarbonyl-containing compounds (A2-2) include thiocarbonyl-containing compounds corresponding to the carbonyl-containing compounds (A2-1).

The imines (A2-3) include imines (inclusive of oximes and hydrazones) each derived from one of the carbonyl-containing compound (A2-1) with ammonia or an amine. Examples of the amine include amines such as methylamine, ethylamine, propylamine, butylamine, hexylamine, benzylamine, cyclohexylamine, and aniline; hydroxylamines such as hydroxylamine and O-methylhydroxylamine; and hydrazines such as hydrazine, methylhydrazine, and phenylhydrazine.

The compounds (A3) each having a methine carbon atom include, for example, (A3-1) cyclic compounds each having a methine group (i.e., a methine carbon-hydrogen bond) as a constitutional unit of their ring and (A3-2) chain compounds each having a methine carbon atom.

The cyclic compounds (A3-1) include, for example, (A3-1a) bridged compounds each having at least one methine group and (A3-1b) non-aromatic cyclic compounds each having a hydrocarbon group combined with their ring (e.g., alicyclic hydrocarbons). The bridged compounds also include compounds each containing two rings commonly possessing two carbon atoms, such as hydrogenated products of condensed polycyclic aromatic hydrocarbons.

Examples of the bridged cyclic compounds (A3-1a) include bridged cyclic hydrocarbons or bridged heterocyclic compounds each having two to four rings, such as decalin, bicyclo[2.2.2]octane, bicyclo[3.3.3]undecane, bornane, bornylene, norbornane, norbornene, tricyclo[5.2.1.0$^{3,8}$]decane, tricyclo[4.2.1.1$^{2,5}$]decane, exotricyclo[5.2.1.0$^{2,6}$]decane, endotricyclo[5.2.1.0$^{2,6}$]decane, endotricyclo[5.2.2.0$^{2,}$ $^{6}$]undecane, adamantane, 1-adamantanol, 1,3-dimethyladamantane, 1-carboxyadamantane, 1-methoxycarbonyladamantane, 1-nitroadamantane, and quinuclidine, and derivatives of them. These bridged cyclic compounds each have a methine carbon atom at a bridgehead position (corresponding to a junction position when two rings commonly possess two atoms).

The non-aromatic cyclic compounds (A3-1b) each having a hydrocarbon group bonded to their ring include, for example, alicyclic hydrocarbons which have about three to about fifteen members and have a hydrocarbon group (e.g., an alkyl group) having about one to about twenty carbon atoms (preferably having about one to about ten carbon atoms) bonded to their ring, and derivatives thereof, such as 1-methylcyclopentane, 1-methylcyclohexane, limonene, menthene, menthol, carbomenthone, and menthone. The non-aromatic cyclic compounds (A3-1b) each having a hydrocarbon group bonded to their ring each have a methine carbon atom at the bonding position between the ring and the hydrocarbon group.

The chain compounds (A3-2) each having a methine carbon atom include, for example, chain hydrocarbons each having a tertiary carbon atom, including aliphatic hydrocarbons having about four to about twenty carbon atoms, preferably about four to about ten carbon atoms, and derivatives thereof, such as isobutane, isopentane, isohexane, 3-methylpentane, 2,3-dimethylbutane, 2-methylhexane, 3-methylhexane, 3,4-dimethylhexane, and 3-methyloctane.

The compounds (A4) each having a carbon-hydrogen bond at the adjacent position to an unsaturated bond include, for example, (A4-1) aromatic compounds each having methyl group or methylene group at the adjacent position to an aromatic ring (at the "benzylic position") and (A4-2) non-aromatic compounds each having methyl group or methylene group at the adjacent position to an unsaturated bond (e.g., a carbon-carbon unsaturated bond or a carbon-oxygen double bond).

In the aromatic compounds (A4-1), the aromatic rings may be any of aromatic hydrocarbon rings and aromatic heterocyclic rings. Examples of the aromatic hydrocarbon rings include benzene ring; and fused carbocyclic rings including fused carbocyclic rings each including fused two to ten carbocyclic rings each having four to seven members, such as naphthalene, azulene, indacene, anthracene, phenanthrene, triphenylene, and pyrene. Examples of the aromatic heterocyclic rings include heterocyclic rings each having oxygen atom as heteroatom, including five-membered rings such as furan, oxazole, and isoxazole, six-membered rings such as 4-oxo-4H-pyran, and fused rings such as benzofuran, isobenzofuran, and 4-oxo-4H-chromene; heterocyclic rings containing sulfur atom as heteroatom, including five-membered rings such as thiophene, thiazole, isothiazole, and thiadiazole, six-membered rings such as 4-oxo-4H-thiopyran, and fused rings such as benzothiophene; and heterocyclic rings containing nitrogen atom as heteroatom, including five-membered rings such as pyrrole, pyrazole, imidazole, and triazole, six-membered rings such as pyridine, pyridazine, pyrimidine, and pyrazine, and fused rings such as indole, quinoline, acridine, naphthyridine, quinazoline, and purine.

The methylene group at the adjacent position to the aromatic ring may be a methylene group constituting a non-aromatic ring fused with the aromatic ring. The aromatic compounds (A4-1) may have both methyl group and methylene group at the adjacent position to the aromatic ring.

Examples of the aromatic compounds each having methyl group at the adjacent position to an aromatic ring include aromatic hydrocarbons each having from about one to about six methyl groups substituted on the aromatic ring, such as toluene, xylenes, 1-ethyl-4-methylbenzene, 1-ethyl-3-methylbenzene, 1-isopropyl-4-methylbenzene, 1-t-butyl-4-methylbenzene, 1-methoxy-4-methylbenzene, mesitylene, pseudocumene, durene, methylnaphthalene, dimethylnaphthalene, methylanthracene, 4,4'-dimethylbiphenyl, tolualdehyde, dimethylbenzaldehyde, trimethylbenzaldehyde, toluic acid, trimethylbenzoic acid, and dimethylbenzoic acid; and heterocyclic compounds each having from about one to about six methyl groups substituted on their heterocyclic ring, such as 2-methylfuran, 3-methylfuran, 3-methylthiophene, 2-methylpyridine, 3-methylpyridine, 4-methylpyridine, 2,4-dimethylpyridine, 2,4,6-trimethylpyridine, 4-methylindole, 2-methylquinoline, and 3-methylquinolin.

Examples of the aromatic compounds each having methylene group at the adjacent position to an aromatic ring include aromatic hydrocarbons each having an alkyl group or substituted alkyl group containing two or more carbon atoms, such as ethylbenzene, propylbenzene, 1,4-diethylbenzene, and diphenylmethane; aromatic heterocyclic compounds each having an alkyl group or substituted alkyl group containing two or more carbon atoms, such as 2-ethylfuran, 3-propylthiophene, 4-ethylpyridine, and 4-butylquinoline; and compounds each having a non-aromatic ring condensed with an aromatic ring, which non-aromatic ring has methylene group at the adjacent position to the aromatic ring, such as dihydronaphthalene, indene, indan, tetralin, fluorene, acenaphthene, phenalene, indanone, and xanthene.

The non-aromatic compounds (A4-2) each having methyl group or methylene group at the adjacent position to an unsaturated bond include, for example, (A4-2a) chain unsaturated hydrocarbons each having methyl group or methylene group at an "allylic position", and (A4-2b) compounds each having methyl group or methylene group at the adjacent position to a carbonyl group.

Examples of the chain unsaturated hydrocarbons (A4-2a) include chain unsaturated hydrocarbons each having about three to about twenty carbon atoms, such as propylene, 1-butene, 2-butene, 1-pentene, 1-hexene, 2-hexene, 1,5-hexadiene, 1-octene, 3-octene, and undecatriene. The compounds (A4-2b) include, for example, ketones including chain ketones such as acetone, methyl ethyl ketone, 3-pentanone, and acetophenone, and cyclic ketones such as cyclohexanone; carboxylic acids and derivatives thereof, such as acetic acid, propionic acid, butanoic acid, pentanoic acid, hexanoic acid, heptanoic acid, phenylacetic acid, malonic acid, succinic acid, glutaric acid, and esters of them.

The non-aromatic cyclic hydrocarbons (A5) include cycloalkanes (A5-1) and cycloalkenes (A5-2).

Examples of the cycloalkanes (A5-1) include compounds each having a three- to thirty-membered cycloalkane ring, such as cyclopentane, cyclohexane, cyclooctane, cyclodecane, cyclododecane, and derivatives thereof. Preferred cycloalkane rings include five- to thirty-membered cycloalkane rings, of which five- to twenty-membered cycloalkane rings are more preferred.

Examples of the cycloalkenes (A5-2) include compounds each having a three- to thirty-membered cycloalkene ring, such as cyclopentene and cyclohexene; cycloalkadienes such as cyclopentadiene, 1,3-cyclohexadiene, and 1,5-cyclooctadiene; cycloalkatrienes such as cyclooctatriene; and derivatives of them. Preferred cycloalkenes include compounds each having a three- to twenty-membered ring, of which those having a three- to twelve-membered ring are more preferred.

The conjugated compounds (A6) include, for example, (A6-1) conjugated dienes, (A6-2) α,β-unsaturated nitriles, and (A6-3) α,β-unsaturated carboxylic acids or derivatives thereof (e.g., esters, amides, and acid anhydrides).

The conjugated dienes (A6-1) include, for example, butadiene, isoprene. The "conjugated dienes (A6-1)" herein further include compounds each having a double bond and a triple bond conjugated with each other, such as vinylacetylene.

Examples of the α,β-unsaturated nitriles (A6-2) include (meth)acrylonitriles. Examples of the α,β-unsaturated carboxylic acids and derivatives thereof (A6-3) include (meth)acrylic acids; (meth)acrylic esters such as methyl (meth)acrylates, ethyl(meth)acrylates, isopropyl (meth)acrylates, butyl (meth)acrylates, and 2-hydroxyethyl (meth)acrylates; and (meth)acrylamide derivatives such as (meth)acrylamides and N-methylol(meth)acrylamides.

Examples of the amines (A7) include primary or secondary amines including aliphatic amines such as methylamine, ethylamine, propylamine, butylamine, dimethylamine, diethylamine, dibutylamine, ethylenediamine, 1,4-butanediamine, hydroxylamine, and ethanolamine; alicyclic amines such as cyclopentylamine and cyclohexylamine; aromatic amines such as benzylamine and toluidine; cyclic amines to which an aromatic or non-aromatic ring may be fused, such as pyrrolidine, piperidine, piperazine, and indoline.

Examples of the aromatic hydrocarbons (AB) include aromatic compounds each having at least one benzene ring, such as benzene, naphthalene, acenaphthylene, phenanthrene, anthracene, naphthacene, aceanthrylene, triphenylene, pyrene, chrysene, naphthacene, picene, perylene, pentacene, coronene, pyranthrene, and ovalene. Of these aromatic hydrocarbons, preferred are fused polycyclic aromatic compounds each having two or more (e.g., two to ten) fused benzene rings. These aromatic hydrocarbons may each have one substituent or two or more substituents. With each of the benzene rings, a non-aromatic carbon ring, an aromatic heterocyclic ring or a non-aromatic heterocyclic ring may be fused.

Examples of the straight-chain alkanes (A9) include straight-chain alkanes each having about one to about thirty carbon atoms, such as methane, ethane, propane, butane, pentane, hexane, heptane, octane, nonane, decane, dodecane, tetradecane, and hexadecane, of which those having about one to about twenty carbon atoms are preferred.

The olefins (A10) may be whichever of α-olefins and internal olefins each of which may be substituted and also include dienes and other olefins each having two or more carbon-carbon double bonds. Examples of substituents herein are the above-exemplified substituents such as hydroxyl group and acyloxy groups. Examples of the olefins (A10) include chain olefins such as ethylene, propylene, 1-butene, 2-butene, isobutene, 1-pentene, 2-pentene, 1-hexene, 2-hexene, 2,3-dimethyl-2-butene, 3-hexene, 3-hexen-1-ol, 1-octene, 2-octene, 3-octene, 4-octene, 1-decene, 1-dodecene, styrene, vinyltoluene, α-methylstyrene, 3-vinylpyridine, and 3-vinylthiophene; and cyclic olefins such as cyclopentene, cyclohexene, limonene, 1-p-menthene, 3-p-menthene, and 2-bornene.

Each of these radical-formable compounds can be used alone or in combination, and in the latter case, the compounds used in combination may belong to the same or different categories. When two or more different compounds, especially two or more different compounds belonging to different categories, are used typically in a reaction with oxygen-containing gas such as oxygen gas, one of the substrates acts as a co-reacting agent (e.g., co-oxidizing agent) with respect to the other and may thereby yield a significantly increased reaction rate in some cases.

[Radical-Scavenging Compounds (B)]

The radical-scavenging compounds (B) may be any compounds, as long as they can form a stable compound as a result of the reaction with a free radical. Representative examples of such compounds (B) include (B1) unsaturated compounds, (B2) compounds each having a methine carbon atom, (B3) heteroatom-containing compounds, and (B4) oxygen-containing reacting agents (e.g., oxygen-containing gases). Each of these compounds may be used alone or in combination. These compounds may each have one or more various substituents, within ranges not adversely affecting the reaction.

The unsaturated compounds (B1) include a wide variety of compounds each having an unsaturated bond. Examples of such compounds include (B1-1) unsaturated compounds each having an electron attractive group at the adjacent position to a carbon-carbon unsaturated bond [active olefins (electron-deficient olefins) and other active unsaturated compounds], (B1-2) compounds each having a carbon-carbon triple bond, (B1-3) compounds each having an aromatic ring, (B1-4) ketenes, (B1-5) isocyanate or thiocyanate compounds, and (B1-6) inert olefins.

Examples of the active unsaturated compounds (B1-1) include $\alpha,\beta$-unsaturated esters such as methyl (meth)acrylates, ethyl(meth)acrylates, isopropyl (meth)acrylates, phenyl(meth)acrylates, methyl crotonate, methyl 2-pentenoate, methyl cinnamate, dimethyl maleate, diethyl maleate, dimethyl fumarate, diethyl fumarate, methyl 3-cyanoacrylate, and ethyl 3-cyancacrylate; $\alpha,\beta$-unsaturated ketones such as vinyl methyl ketone and vinyl ethyl ketone; $\alpha,\beta$-unsaturated aldehydes such as propenal and crotonaldehyde; $\alpha,\beta$-unsaturated nitrites such as acrylonitrile and methacrylonitrile; $\alpha,\beta$-unsaturated carboxylic acids such as (meth)acrylic acids and crotonic acid; $\alpha,\beta$-unsaturated carboxylic acid amides such as (meth)acrylamides; $\alpha,\beta$-unsaturated imines such as N-(2-propenylidene)methylamine and N-(2-butenylidene) methylamine; compounds, each having an aryl group bonded at the adjacent position to a carbon-carbon unsaturated bond, such as styrene derivatives including styrene, vinyltoluene, $\alpha$-methylstyrene, and $\beta$-methylstyrene and the like; and conjugated dienes (including compounds having a double bond and a triple bond conjugated with each other), such as butadiene, isoprene, 2-chlorobutadiene, 2-ethylbutadiene, vinylacetylene, and cyclopentadiene derivatives.

The compounds (B1-2) each having a carbon-carbon triple bond include, for example, methylacetylene and 1-butyne. The compounds (B1-3) each having an aromatic ring include, for example, compounds each having an aromatic carbocyclic ring such as benzene ring or naphthalene ring; and compounds each having an aromatic heterocyclic ring such as pyrrole ring, furan ring, or thiophene ring. Examples of the ketenes (B1-4) include ketene and 2-methylketene. The isocyanate or thiocyanate compounds (B1-5) include, for example, methyl isocyanate, ethyl isocyanate, phenyl isocyanate, methyl thiocyanate, ethyl thiocyanate, and phenyl thiocyanate.

The inert olefins (B1-6) may be whichever of $\alpha$-olefins and internal olefins and further include dienes and other olefins each having two or more carbon-carbon bonds. Representative examples of the inert olefins (B1-6) include chain olefins (alkenes) such as ethylene, propylene, 1-butene, 2-butene, isobutene, 1-hexene, 2-hexene, 3-hexene, 1-octene, 2-octene, 3-octene, 4-octene, 1-decene, and 1-dodecene; and cyclic olefins (cycloalkenes) such as cyclopentene, cyclohexene, cyclooctene, cyclodecene, and cyclododecene.

The compounds (B2) each having a methine carbon atom include, for example, the compounds exemplified as the compounds (A3). One compound may be used both as a compound (A3) and a compound (B2) in the reaction.

The heteroatom-containing compounds (B3) include, for example, sulfur-containing compounds (B3-1), nitrogen-containing compounds (B3-2), phosphorus-containing compounds (B3-3), and oxygen-containing compounds (B3-4). Examples of the sulfur-containing compounds (B3-1) include sulfides and thiols. The nitrogen-containing compounds (B3-2) include, for example, amines. The phosphorus-containing compounds (B3-3) include, for example, phosphites. The oxygen-containing compounds (B3-4) include, for example, N-oxides.

The oxygen-containing reacting agents (B4) include, for example, oxygen-containing gases; and nitric acid or nitrous acid, and salts of them (hereinafter also referred to as "a nitric acid"). Examples of the oxygen-containing gases include those having a boiling point or sublimation point of 45° C. or lower, and representative examples thereof include (B4-1) oxygen, (B4-2) carbon monoxide, (B4-3) nitrogen oxides, and (B4-4) sulfur oxides. Each of these oxygen-containing reacting agents can be used alone or in combination.

The oxygen (B4-1) may be whichever of molecular oxygen and active oxygen. The molecular oxygen is not specifically limited and can be, for example, pure oxygen, oxygen diluted with an inert gas such as nitrogen, helium, argon or carbon dioxide gas, or air. Molecular oxygen is often used as the oxygen.

The carbon monoxide (B4-2) may be pure carbon monoxide or carbon monoxide diluted with an inert gas. When carbon monoxide is used in combination with oxygen, a carboxylic acid can be obtained in a high yield as a result of the reaction with the compound (A).

The nitrogen oxides (B4-3) include compounds represented by the formula: $N_xO_y$, wherein "x" is 1 or 2; and "y" is an integer of from 1 to 6. In these compounds, "y" is generally an integer of from 1 to 3 when "x" is 1; and "y" is generally an integer of from 1 to 6 when "x" is 2.

Representative examples of the nitrogen oxides include $N_2O$, $NO$, $N_2O_3$, $NO_2$, $N_2O_4$, $N_2O_5$, $NO_3$, and $N_2O_6$. Each of these nitrogen oxides can be used alone or in combination. The nitrogen oxides may be pure substances or mixtures mainly containing a nitrogen oxide. Such mixtures mainly containing a nitrogen oxide can be, for example, waste gases formed in oxidation processes with nitric acid.

Preferred nitrogen oxides include, for example, NO, $N_2O_3$, $NO_2$, and $N_2O_3$. In this connection, $N_2O_3$ can be easily obtained upon a reaction of dinitrogen monoxide ($N_2O$) and/or nitrogen monoxide (NO) with oxygen. More specifically, $N_2O_1$ can be prepared by introducing dinitrogen monoxide (or nitrogen monoxide) and oxygen into a cooled reactor to yield a blue liquid $N_2O_3$. Accordingly, a reaction according to the present invention can be performed by introducing dinitrogen monoxide ($N_2O$) and/or nitrogen monoxide (NO) and oxygen into a reaction system without the previous formation of $N_2O_3$. The nitrogen oxide can be used in combination with oxygen. For example, by using $NO_2$ in combination with oxygen, the yield of the product (e.g., a nitro compound) can further be improved.

The sulfur oxides (B4-4) include compounds represented by the formula: $S_pO_q$, wherein "p" is 1 or 2; and "q" is an integer of from 1 to 7. In these compounds, "q" is generally an integer of from 1 to 4 when "p" is 1; and "q" is generally 3 or 7 when "p" is 2.

Representative examples of the sulfur oxides include SO, $S_2O_3$, $SO_2$, $SO_3$, $S_2O_7$, and $SO_4$. Each of these sulfur oxides can be used alone or in combination. Fuming sulfuric acid containing sulfur trioxide can be employed as the sulfur trioxide.

Preferred sulfur oxides include those mainly containing at least one of sulfur dioxide ($SO_2$) and sulfur trioxide ($SO_3$). The sulfur oxide can be used in combination with oxygen. By using sulfur dioxide ($SO_2$), for example, in combination with oxygen, a corresponding sulfonic acid can be obtained in a high yield as a result of the reaction with the compound (A).

The salts of nitric acid or nitrous acid include, for example, alkali metal salts such as sodium salts and potassium salts; alkaline earth metal salts such as magnesium salts, calcium salts, and barium salts; and salts of other metals, such as silver salts, aluminium salts, and zinc salts. Preferred salts include alkali metal salts of nitric acid or nitrous acid.

The nitric acid can be supplied as intact to the reaction system or may be supplied in the form of a solution such as an aqueous solution. Alternatively, this component may be formed in the reaction system before reaction.

A reaction between a radical-formable compound (A) and a radical-scavenging compound (B) is carried out in the presence of, or in the absence of, a solvent. Examples of the solvent include organic acids such as acetic acid and propionic acid; nitrites such as acetonitrile, propionitrile, and benzonitrile; amides such as formamide, acetamide, dimethylformamide (DMF), and dimethylacetamide; aliphatic hydrocarbons such as hexane and octane; halogenated hydrocarbons such as chloroform, dichloromethane, dichloroethane, carbon tetrachloride, chlorobenzene, and trifluoromethylbenzene; nitro compounds such as nitrobenzene, nitromethane, and nitroethane; esters such as ethyl acetate and butyl acetate; water; and mixtures of these solvents. Frequently used solvents herein include organic acids such as acetic acid; nitriles such as acetonitrile and benzonitrile; halogenated hydrocarbons such as trifluoromethylbenzene; and esters such as ethyl acetate.

The ratio of the radical-formable compound (A) to the radical-scavenging compound (B) can be appropriately set depending on the types (costs and reactivities) and the combination of the two compounds. For example, the compound (A) may be used in excess (e.g., from about 2 to about 50 times by mole) to the compound (B). Contrarily, the compound (B) may be used in excess to the compound (A).

A reaction temperature can be appropriately set depending on the types of the compound (A) and compound (B) or the type of the target product, and is, for example, from about 0° C. to about 300° C., preferably from about 20° C. to about 250° C., and more preferably from about 20° C. to about 200° C. The reaction can be performed at atmospheric pressure or under a pressure (under a load). When the reaction is performed under a pressure, the pressure (load) is usually from about 0.1 to about 10 MPa, for example, from about 0.15 to about 8 MPa, and preferably from about 1 to about 8 MPa. A reaction time can be appropriately set within a range of, for example, from about 10 minutes to about 48 hours according to the reaction temperature and pressure.

The reaction can be performed according to a common system such as a batch system, semi-batch system, or continuous system. By adding the catalyst including a compound having a dicarboximide skeleton to the reaction system in installments, the target compound can be obtained with a higher conversion or selectivity in many cases.

According to a method of the present invention, there is produced an addition or substitution reaction product or a derivative thereof, in accordance with the combination of the radical-formable compound (A) and the radical-scavenging compound (B). Such addition or substitution reaction products include, for example, carbon-carbon bonded products (e.g., coupling reaction products), oxidation products, carboxylation products, nitration products, and sulfonation products.

When a heteroatom-containing compound (A1) having a carbon-hydrogen bond at the adjacent position to the heteroatom, for example, is used as the compound (A), the adjacent position to the heteroatom is bonded to an atom (e.g., carbon atom) constituting an unsaturated bond of the unsaturated compound (B1), to the methine carbon atom of the compound (B2) having a methine carbon atom, or to the heteroatom of the heteroatom-containing compound (B3) and thereby yields an addition or substitution reaction product or a derivative thereof.

When a compound (A2) having a carbon-heteroatom double bond, such as a carbonyl-group-containing compound, is used as the compound (A), the bond between a carbon atom involved in the carbon-heteroatom double bond (e.g., a carbonyl carbon atom) and an atom adjacent to the carbon atom is cleaved, and an atomic group containing the carbon-heteroatom double bond (e.g., an acyl group) is bonded to the above-mentioned position of the compound (B1), (B2) or (B3) to yield an addition or substitution reaction product or a derivative thereof.

When a compound (A3) having a methine carbon atom is used as the compound (A), the methine carbon atom is bonded to the above-mentioned position of the compound (B3), (B2) or (B3) to yield an addition or substitution reaction product or a derivative thereof.

Generally, the use of an unsaturated compound (B1) as the radical scavenging compound (B) yields an addition reaction product, and the use of a compound (B2) having a methine carbon atom as the compound (B) yields a substitution reaction product such as a coupling product.

A reaction between an oxygen-containing reacting agent (B4) as the radical scavenging compound (B) with the compound (A) yields an organic compound having an oxygen-containing group (e.g., hydroxyl group, oxo group, carboxyl group, nitro group, or sulfur acid group) according to the type of the oxygen-containing reacting agent.

More specifically, when oxygen (B4-1) is used as the oxygen-containing reacting agent, an oxidation reaction proceeds to yield a corresponding oxidation product. When a heteroatom-containing compound (A1) having a carbon-hydrogen bond at the adjacent position to the heteroatom, for example, is used as the compound (A), the carbon atom at the adjacent position to the heteroatom is oxidized. For example, a primary alcohol yields a corresponding aldehyde or carboxylic acid; and a secondary alcohol yields, for example, a corresponding ketone. A 1,3-diol yields a corresponding hydroxyketone; and a 1,2-diol yields a corresponding carboxylic acid as a result of oxidative cleavage. An ether yields a corresponding ester or acid anhydride.

A compound (A2) having a carbon-heteroatom double bond, when used as the compound (A), yields an oxidation product according typically to the type of the heteroatom. For example, when a ketone is oxidized, a carboxylic acid and the like is produced as a result of cleavage; and, for example, a cyclic ketone such as cyclohexanone yields a dicarboxylic acid such as adipic acid. For example, by using a heteroatom-containing compound (A1) having a carbon-hydrogen bond at the adjacent position to the heteroatom such as a secondary alcohol (e.g., benzhydrol) as a co-reacting agent (co-oxidizing agent), a Baeyer-Villiger type reaction proceeds under mild conditions. As a result, a cyclic ketone yields a corresponding lactone, and a chain ketone yields a corresponding ester in high yields respectively. In addition, an aldehyde yields a corresponding carboxylic acid.

A compound (A3) having a methine carbon atom, when used as the compound (A), can yield an alcohol derivative having a hydroxyl group introduced into the methine carbon in a high yield. For example, oxidation of a bridged hydrocarbon (A3-1a) such as adamantane yields alcohol derivatives having a hydroxyl group at a bridgehead position, such as 1-adamantanol, 1,3-adamantanediol, and 1,3,5-adamantanetriol, with a high selectivity. A chain compound (A3-2) having a methine carbon atom, such as isobutane, can yield a tertiary alcohol, such as t-butanol, in a high yield.

When a compound (A4) having a carbon-hydrogen bond at the adjacent position to an unsaturated bond is used as the compound (A), the adjacent position to the unsaturated bond is efficiently oxidized to yield, for example, an alcohol, a carboxylic acid, and/or a ketone. A compound having methyl group at the adjacent position to an unsaturated bond, for example, yields a primary alcohol or carboxylic acid in a high yield. Likewise, a compound having methylene group or methine group at the adjacent position to an unsaturated bond may yield a secondary or tertiary alcohol, ketone, and/or carboxylic acid in a high yield, according to reaction conditions.

More specifically, an aromatic compound having an alkyl group or a lower-order oxidized group thereof bonded to its aromatic ring yields an aromatic carboxylic acid having a carboxyl group bonded to the aromatic ring as a result of oxidation of the alkyl group or the lower-order oxidized group thereof. This reaction will be illustrated below.

Examples of the aromatic ring include aromatic carbocyclic rings such as benzene ring, naphthalene ring, acenaphthylene ring, phenanthrene ring, anthracene ring, and pyrene ring; and aromatic heterocyclic rings each having about one to about three of at least one heteroatom selected from oxygen atom, sulfur atom, and nitrogen atom, such as furan ring, thiophene ring, pyrrole ring, pyrazole ring, imidazole ring, tetrazole ring, oxazole ring, isoxazole ring, isothiazole ring, thiazole ring, pyridine ring, 4-oxo-1,4-dihydropyridine ring, 2-oxo-1,2-dihydropyridine ring, pyridazine ring, pyrimidine ring, pyrazine ring, quinoline ring, 4-oxo-4H-pyran ring, 2-oxo-2H-pyran ring, benzofuran ring, indole ring, indazole ring, benzotriazole ring, quinazoline ring, phthalazine ring, 1,8-naphthyridine ring, acridine ring, phenazine ring, and chromone ring. These aromatic rings may each have one or more various substituents within ranges not adversely affecting the reaction. An aromatic ring or non-aromatic ring may be fused. Examples of the substituents herein include carboxyl group, halogen atoms, hydroxyl group, alkoxy groups, acyloxy groups, substituted oxycarbonyl groups, substituted or unsubstituted amino groups, and nitro group. Examples of the alkyl group bonded to the aromatic ring include primary or secondary alkyl groups, such as methyl, ethyl, propyl, isopropyl, butyl, isobutyl, s-butyl, pentyl, isopentyl, hexyl, isohexyl, heptyl, octyl, 2-ethylhexyl, and decyl groups. Among them, an alkyl group having one to four carbon atoms is preferred, of which an alkyl group having one to three carbon atoms, such as methyl group, ethyl group, or isopropyl group is preferred.

The term "lower-order oxidized group of an alkyl group" herein means a lower-order oxidized group whose carbon atom at the 1-position is not yet oxidized into carboxyl group or an equivalent thereof. The lower-order oxidized group includes, for example, hydroxyalkyl groups, formyl group, formylalkyl groups, and alkyl groups having an oxo group. Examples of the hydroxyalkyl groups include hydroxymethyl, 1-hydroxyethyl, 2-hydroxyethyl, 1-hydroxypropyl, 1-hydroxy-1-methylethyl, 2-hydroxypropyl, 3-hydroxypropyl, and 1-hydroxybutyl groups. Examples of the formylalkyl groups include formylmethyl, 1-formylethyl, 2-formylethyl, and 1-formylpropyl groups. Examples of the alkyl groups each having an oxo group include aliphatic acyl groups such as acetyl, propionyl, butyryl, pentanoyl, and hexanoyl groups. Among them, lower-order oxidized groups corresponding to alkyl groups having one to four carbon atoms are preferred, of which those corresponding to alkyl groups having one to three carbon atoms are more preferred. The alkyl groups and lower-order oxidized groups thereof may each have one or more substituents within ranges not adversely affecting the reaction.

Representative examples of the aromatic compound to whose aromatic ring an alkyl group or a lower-order oxidized group thereof is bonded include compounds to whose aromatic ring one alkyl group or lower-order oxidized group thereof is bonded, such as toluene, ethylbenzene, isopropylbenzene (cumene), n-propylbenzene, o-cresol, m-cresol, p-cresol, o-toluic acid (2-methylbenzoic acid), m-toluic acid (3-methylbenzoic acid), p-toluic acid (4-methylbenzoic acid), 4-chloro-1-methylbenzene, 2-methoxy-1-methylbenzene, 3-methoxy-1-methylbenzene, 4-methoxy-1-methylbenzene, 4-ethoxy-1-methylbenzene, 4-isopropoxy-1-methylbenzene, 2-acetoxy-1-methylbenzene, 3-acetoxy-1-methylbenzene, 4-acetoxy-1-methylbenzene, 4-propionyloxy-1-methylbenzene, 4-methoxycarbonyl-1-methylbenzene, 4-ethoxycarbonyl-1-methylbenzene, 4-amino-1-methylbenzene, 4-dimethylamino-1-methylbenzene, 1-methylnaphthalene, 2-methylnaphthalene, methylanthracene, benzyl alcohol, 1-hydroxyethylbenzene, benzaldehyde, acetophenone, propiophenone, o-carboxybenzaldehyde, m-carboxybenzaldehyde, p-carboxybenzaldehyde, o-hydroxybenzaldehyde, m-hydroxybenzaldehyde, p-hydroxybenzaldehyde, o-hydroxybenzyl alcohol, m-hydroxybenzyl alcohol, p-hydroxybenzyl alcohol, 2-methylfuran, 3-methylfuran, 2-methylthiophene, 3-methylthiophene, 2-methylpyridine (α-picoline), 3-methylpyridine (β-picoline), 4-methylpyridine (γ-picoline), 2-ethylpyridine, 3-ethylpyridine, 4-ethylpyridine, 3-isopropylpyridine, 4-methylindole, 5-methylindole, 7-methylindole, 2-methylquinoline, 3-methyl-4-pyrone, N-substituted or unsubstituted 3-methyl-4-pyridone, and 2-chloro-4-methylpyridine; compounds to whose aromatic ring two groups selected from alkyl groups and lower-order oxidized groups thereof are bonded, such as o-xylene, m-xylene, p-xylene, 1-ethyl-4-methylbenzene, 1-ethyl-3-methylbenzene, diisopropylbenzene, xylenols (e.g., 2,3-xylenol, 2,4-xylenol, and 3,5-xylenol), thymol (6-isopropyl-m-cresol), methylbenzaldehyde (tolualdehyde), dimethylbenzoic acids (e.g., 2,3-dimethylbenzoic acid, 2,4-dimethylbenzoic acid, and 3,5-dimethylbenzoic acid), 4,5-dimethylphthalic acid, 4,6-dimethylisophthalic acid, 2,5-dimethylterephthalic acid, 3,4,5,6-tetrachloro-1,2-dimethylbenzene, 3,4,5,6-tetrabromo-1,2-dimethylbenzene, 2,3-dimethylnitrobenzene, 1,5-dimethylnaphthalene, 2,5-dimethylnaphthalene, diisopropylnaphthalene, dimethylanthracene, 4,4'-dimethylbiphenyl, 2,3-dimethylpyridine (2,3-lutidine), 2,4-dimethylpyridine (2,4-lutidine), 2,5-dimethylpyridine (2,5-lutidine), 3,5-dimethylpyridine (3,5-lutidine), 2,6-dimethylpyridine (2,6-lutidine), 2-ethyl-4-methylpyridine, 3,5-dimethyl-4-pyrone, and N-substituted or unsubstituted 3,5-dimethyl-4-pyridone; and compounds to whose aromatic ring three or more groups selected from alkyl groups and lower-order oxidized groups thereof are bonded, such as 1,2,3-trimethylbenzene, 1,2,4-trimethylbenzene (pseudocumene), 1,3,5-trimethylbenzene (mesitylene), 1,2,3,5-tetramethylbenzene, 1,2,3,4-tetramethylbenzene, 1,2,4,5-tetramethylbenzene (durene), 1,2,3,4,5,6-hexamethylbenzene, dimethylbenzyl alcohol, dimethylbenzaldehyde, 2,4,5-trimethylbenzoic acid, trimethylanthracene, 2,3,4-trimethylpyridine, 2,3,5-trimethylpyridine, 2,3,6-trimethylpyridine, and 2,4,6-trimethylpyridine.

According to the present invention, products are obtained in good yields, respectively. For example, there is produced benzoic acid from toluene, ethylbenzene, isopropylbenzene, benzaldehyde, or a mixture of these compounds; terephthalic acid from p-xylenes, p-isopropyltoluene, p-diisopropylbenzene, p-tolualdehyde, p-toluic acid, p-carboxybenzaldehyde, or a mixture of these compounds; isophthalic acid from m-xylenes, m-tolualdehyde, m-carboxybenzaldehyde, or a mixture of these compounds; phthalic acid from o-xylenes; trimellitic acid from pseudocumene, dimethylbenzaldehyde, dimethylbenzoic acid, or a mixture of these compounds; pyromellitic acid from durene, trimethylbenzaldehyde, trimethylbenzoic acid, or a mixture of these compounds; and 3-quinolinecarboxylic acid typically from 3-methylquinoline in good yields. In addition, nicotinic acid is available from β-picoline.

A compound having methylene group at the adjacent position to a carbon-carbon double bond, for example, yields a secondary alcohol or ketone. In this case, by using, as the promoter, a cobalt(II) salt of an acid having a pKa of 8.0 or less, such as cobalt(II) acetate or cobalt(II) nitrate, a corresponding conjugated unsaturated carbonyl compound having an oxo group introduced into the carbon atom of the methylene group can be obtained in a high yield. More specifically, nootkatone is available from valencene in a high yield.

By using a non-aromatic cyclic hydrocarbon (A5) as the compound (A), an alcohol, hydroperoxide, or ketone having a hydroxyl group, hydroperoxy group or oxo group introduced into a carbon atom constituting its ring is obtained. Under some reaction conditions, the ring is oxidatively cleaved to yield a corresponding dicarboxylic acid. For example, cyclohexane can yield cyclohexyl alcohol, cyclohexyl peroxide, cyclohexanone, or adipic acid with high selectivity under appropriately selected conditions. Likewise, a cycloalkane such as cyclohexane yields a bis(1-hydroxycycloalkyl) peroxide such as bis(1-hydroxycyclohexyl) peroxide. By using a strong acid as the promoter, adamantane yields adamantanone in a high yield.

When a conjugated compound (A6) is used as the compound (A), a variety of compounds is formed depending on the structure of the conjugated compound. A conjugated diene yields, for example, an alkenediol as a result of oxidation. Specifically, butadiene yields, for example, 2-butene-1,4-diol and/or 1-butene-3,4-diol as a result of oxidation. When an α,β-unsaturated nitrile, or α,β-unsaturated carboxylic acid or a derivative thereof is oxidized, the α,β-unsaturated bonding position is selectively oxidized and is converted into a single bond, and the β-position is converted into a formyl group, an acetal group (in a reaction in the presence of an alcohol) or an acyloxy group (in a reaction in the presence of a carboxylic acid) in the resulting compound. More specifically, for example, oxidation of acrylonitrile and methyl acrylate in the presence of methanol yields 3,3-dimethoxypropionitrile and methyl 3,3-diethoxypropionate, respectively.

When an amine (A7) is used as the compound (A), a corresponding Schiff base or oxime, for example, is formed. When an aromatic compound (A8) is used as the compound (A) in the co-existence typically of a compound (A4) having a carbon-hydrogen bond at the adjacent position to an unsaturated bond, (e.g., fluorene) as the co-reacting agent (co-oxidizing agent), a corresponding quinone is formed in a good yield. A straight-chain alkane (A9) yields, for example, an alcohol, a ketone, and/or a carboxylic acid.

By using an olefin (A10) as the compound (A), a corresponding epoxy compound can be obtained. In this case, an epoxidation reaction proceeds under mild conditions and thereby yields the corresponding epoxide in a good yield when a heteroatom-containing compound (A1) having a carbon-hydrogen bond at the adjacent position to the heteroatom, such as a secondary alcohol, or a compound (A4) having a carbon-hydrogen bond at the adjacent position to an unsaturated bond is in coexistence as the co-reacting agent (co-oxidizing agent).

A corresponding lactam is obtained by allowing at least one compound selected from cycloalkanes, cycloalkanols, and cycloalkanones to react with ammonia and oxygen (B4-1) as the oxygen-containing reacting agent in the presence of the nitrogen-containing cyclic compound catalyst. More specifically, ε-caprolactam is obtained by allowing at least one compound selected from cyclohexane, cyclohexanol, and cyclohexanone to react with ammonia and oxygen in the presence of the catalyst.

When carbon monoxide (B4-2) and oxygen (B4-1) are used as the oxygen-containing reacting agents, a carboxylation reaction smoothly proceeds and thereby yields a corresponding carboxylic acid in a good yield. For example, when a compound (A3) having a methine carbon atom is used as the compound (A), a carboxyl croup is introduced into the methine carbon atom. Likewise, in a compound (A4) having a carbon-hydrogen bond at the adjacent position to an unsaturated bond, a carboxyl group is introduced into a carbon atom involved in the carbon-hydrogen bond. A non-aromatic cyclic hydrocarbon (A5), such as cyclohexane, yields a carboxylic acid having a carboxyl group combined with a carbon atom constituting a ring.

When a nitrogen oxide (B4-3) is used as the oxygen-containing reacting agent, a nitration reaction predominantly proceeds and thereby yields, for example, a corresponding nitro compound. For example, when a compound (A3) having a methine carbon atom is used as the compound (A), the methine carbon atom is nitrated. Likewise, when a compound (A4) having a carbon-hydrogen bond at the adjacent position to an unsaturated bond is used, a carbon atom involved in the carbon-hydrogen bond is nitrated. A non-aromatic cyclic hydrocarbon (A5), such as cyclohexane, yields a corresponding cyclic nitro compound having a nitro group bonded to a carbon atom constituting a ring. Even a straight-chain alkane (A9), such as hexane, can yield a corresponding nitroalkane. When nitrogen dioxide is used as the oxygen-containing reacting agent, the nitration reaction can efficiently proceed by using the substrate in excess to nitrogen dioxide.

When a compound having methyl group at the adjacent position to an aromatic ring (at the "benzylic position"), such as toluene, is used as the compound (A), a nitro group is introduced into the carbon atom of the methyl group. Under some conditions, the methyl group is converted into a formyl group to yield a corresponding aromatic aldehyde (e.g., benzaldehyde), or a nitro group is introduced into the aromatic ring in the resulting compound. The use of a compound having methylene group at the adjacent position to an aromatic ring (e.g., ethylbenzene) as the substrate yields a nitro compound (e.g., α-nitroethylbenzene), in which the methylene group is nitrated; and under some reaction conditions, an oxime compound (e.g., acetophenone oxime) is formed in which the methylene group is converted into an oxime.

By using nitrogen monoxide as the oxygen-containing reacting agent, an ether yields a corresponding aldehyde as a result of cleavage of the ether bond. For example, phthalan yields phthalaldehyde in a high yield. Likewise, by using nitrogen monoxide as the oxygen-containing reacting agent, a cycloalkane yields a corresponding cycloalkanone oxime. For example, cyclohexane yields cyclohexanone oxime.

A corresponding amide or lactam is obtained when a chain or cyclic compound having methylene group is allowed to react with the nitrogen oxide such as nitrogen monoxide in the presence of the nitrogen-containing cyclic compound and a halogen (e.g., chlorine) or a Beckmann rearrangement catalyst. For example, cyclohexane yields ε-caprolactam.

When the nitric acid is used as the oxygen-containing reacting agent, a nitration reaction predominantly proceeds and thereby yields, for example, a corresponding nitro compound, as in the use of the nitrogen oxide (B4-3). For example, when a compound (A4) having a carbon-hydrogen bond at the adjacent position to an unsaturated bond is used as the substrate, a carbon atom involved in the carbon-hydrogen bond is nitrated. When a compound (A3) having a methine carbon atom is used as the substrate, the methine carbon atom is nitrated. When the non-aromatic cyclic hydrocarbon (A5) is used as the substrate, a nitro group is introduced into a carbon atom constituting a ring. In this case, a cycloalkane, such as cyclohexane, yields a corresponding nitrocycloalkane. In the non-aromatic heterocyclic compound having a carbon-hydrogen bond at the adjacent position to the heteroatom, a carbon atom involved in the carbon-hydrogen bond is nitrated. Likewise, the straight-chain alkane (A9), such as hexane, yields a corresponding nitroalkane. This reaction is supposed to proceed in the following manner. The nitrogen-containing cyclic compound catalyst reacts with the nitric acid and thereby yields an imido-N-oxy radical, the radical withdraws a hydrogen atom from the substrate and thereby yields another radical, and to the resulting radical, nitrogen dioxide formed in the reaction system is added and thereby yields a corresponding nitro compound.

When a sulfur oxide (B4-4) is used as the oxygen-containing reacting agent, a sulfonation and/or sulfonation reaction proceeds to yield a corresponding organic sulfur acid or a salt thereof. For example, when a compound (A3) having a methine carbon atom is used as the compound (A), a sulfur acid group is introduced into the methine carbon atom. When a compound (A4) having a carbon-hydrogen bond at the adjacent position to an unsaturated bond is used, a sulfur acid group (e.g., a sulfonic acid group or sulfinic acid group) is introduced into the carbon atom involved in the carbon-hydrogen bond. A non-aromatic cyclic hydrocarbon (A5), such as cyclohexane, yields an organic sulfur acid having a sulfur acid group bonded to a carbon atom constituting the ring. The formed organic sulfur acid can be converted into a corresponding salt thereof according to a common procedure. For example, a corresponding organic sulfur acid salt can be obtained by reacting the organic sulfur acid with an alkali metal hydroxide, alkali metal carbonate, alkali metal hydrogen carbonate, alkaline earth metal hydroxide, alkaline earth metal carbonate, amine, thiourea, or isothiourea in an appropriate solvent such as water.

A complicated organic compound can be obtained through one step in a method according to the present invention, by using two or more types of the radical-formable compounds (A) and/or the radical-scavenging compounds (B) to thereby cause sequential addition or substitution reactions. For example, when an unsaturated compound (B1) and oxygen (B4-1) as the radical scavenging compounds (B) are allowed to react with the compound (A), a group derived from the compound (A) can be bonded to one of the two carbon atoms constituting the unsaturated bond as mentioned above, and a hydroxyl group derived from the oxygen can be introduced into the other carbon atom.

A reaction mechanism in a method according to the present invention is not clarified in detail but is supposed as follows. During the reaction, an oxidative active species [e.g., N-oxy radical (>NO●)] is formed, the oxidative active species withdraws a hydrogen from the compound (A) and allows the compound (A) to form a radical, for example, at the carbon atom at the adjacent position to the heteroatom in the compound (A1), at the carbon atom involved in the carbon-heteroatom double bond in the compound (A2), at the methine carbon atom in the compound (A3), or at the carbon atom at the adjacent position to the unsaturated bond in the compound (A4); the thus-formed radical reacts with the compound (B) and thereby yields a corresponding addition or substitution reaction product. The formed addition or substitution reaction product may further undergo, for example, a dehydration reaction, cyclization reaction, decarboxylation reaction, rearrangement reaction, or isomerization reaction in the reaction system depending on the structure thereof and/or reaction conditions, to thereby yield a corresponding derivative.

According to the present invention, the resulting reaction product is treated with hot water (hydrothermally treated) to thereby decompose and remove components derived from the catalyst. The reaction product to be hydrothermally treated can be any of a reaction mixture after the completion of the reaction; the reaction mixture after a treatment such as extraction, concentration, and/or dilution; and a target compound separated as a result of further treatment such as crystallization, precipitation, and/or distillation. For example, a solid after crystallization or precipitation may be subjected to rinsing and/or repulping with a suitable solvent such as an organic solvent, water, or a mixture of these solvent, and then subjected to hydrothermal treatment. Not a little amount of impurities derived from the catalyst used [catalyst and/or a denatured derivative of the catalyst (deactivated derivative)] is contained in or attached to such a reaction product even after a separation procedure such as crystallization. Such impurities, particularly nitrogen-containing impurities, may adversely affect the quality of product. When an organic compound containing large amounts of these impurities is subjected to a polymerization reaction, the polymerization may be inhibited, or a produced polymer may be colored. According to the present invention, these impurities can be efficiently decomposed to a low-molecular-weight compound such as a gas or a compound highly soluble in water according to a simple procedure. A target compound having a high purity and containing very small amounts of impurities can be obtained by subjecting the reaction product after hydrothermal treatment to a simple separation process. Examples of the low-molecular-weight compound include carbon dioxide, ammonia, nitrogen, nitrogen dioxide, hydroxylamine, and O-substituted hydroxylamines. Examples of the compound highly soluble in water include carboxylic acids and amines.

Of impurities derived from the catalyst, representative examples of denatured derivatives of the catalyst include a compound of Formula (i') wherein Z is hydrogen atom, namely, a compound corresponding to a compound of Formula (i), except with hydrogen atom replacing the —OR group.

More specifically, examples of denatured derivatives of cyclic imide compound catalysts include compounds corresponding to compounds of Formula (1), except with hydrogen atom replacing the —OR group, such as succinimide, α-methylsuccinimide, α,α,-dimethylsuccinimide, α,β-dimethylsuccinimide, α,α,β,β-tetramethylsuccinimide, maleimide, hexahydrophthalimide, cyclohexanetetracarboxylic diimide, phthalimide, tetrabromophthalimide, tetrachlorophthalimide, chlorendimide (HET acid imide), himimide, trimellitimide, pyromellitic diimide, naphthalenetetracarboxylic diimide, α,β-diacetoxysuccinimide, α,β-bis(propionyloxy)succinimide, α,β-bis(valeryloxy)succinimide, α,β-bis(lauroyloxy)succinimide, α,β-bis(benzoyloxy) succinimide, 4-methoxycarbonylphthalimide, 4-chlorophthalimide, 4-ethoxycarbonylphthalimide, 4-pentyloxycarbonylphthalimide, 4-dodecyloxycarbonylphthalimide, 4-phenoxycarbonylphthalimide, 4,5-bis(methoxycarbonyl)phthalimide, 4,5-bis(ethoxycarbonyl)phthalimide, 4,5-bis(pentyloxycarbonyl)phthalimide, 4,5-bis(dodecyloxycarbonyl)phthalimide, 4,5-bis(phenoxycarbonyl)phthalimide, glutarimide, α,α-dimethylglutarimide, β,β-dimethylglutarimide, 1,8-decalindicarboximide, 1,8; 4,5-decalintetracarboxylic diimide, 1,8-naphthalenedicarboximide (cinnaphthalimide), and 1,8; 4,5-naphthalenetetracarboxylic diimide.

Examples of denatured derivatives of cyclic acylurea compound catalysts include compounds corresponding to compounds of Formula (IIa), except with hydrogen atom replacing the —OR group, such as hydantoin and 1-methylhydantoin; compounds corresponding to compounds of Formula (IIb), except with hydrogen atom replacing the —OR group, such as 1,2,4-triazolidine-3,5-dione and 1,2,4-triazoline-3,5-dione; compounds corresponding to compounds of Formula (IIc), except with hydrogen atom replacing the —OR group, such as hexahydro-1,3-diazine-2,4-dione, hexahydro-1,3-diazine-2,4,6-trione, and uracil; compounds corresponding to compounds of Formula (IId), except with hydrogen atom replacing the —OR group, such as hexahydro-1,2,4-triazine-3,5-dione; compounds corresponding to compounds of Formula (IIe), except with hydrogen atom replacing the —OR group, such as hexahydro-1,3,5-triazine-2,4,6-trione (i.e., isocyanuric acid); and compounds corresponding to compounds of Formula (IIf), except with hydrogen atom replacing the —OR group compound, such as hexahydro-1,2,3,5-tetrazine-4,6-dione. Examples of denatured derivatives of isocyanuric acid derivatives represented by Formula (2a), when used as the catalyst, include compounds corresponding to compounds of Formula (2a), except with hydrogen atom replacing at least one of the —OR group, —OR' group, and —OR" group. A compound corresponding to Formula (2a), except with hydrogen atoms replacing all the —OR group, —OR' group, and —OR" group, is isocyanuric acid.

The hydrothermal treatment is carried out by mixing an article to be treated with hot water. The hot water can be any one, as long as it is water at elevated temperatures, and the water herein can be not only pure water but also a water-containing solvent (aqueous solvent) mainly containing water. The content of water in the aqueous solvent is generally 10 percent by weight or more, preferably 30 percent by weight or more, more preferably 50 percent by weight or more, and particularly preferably 80 percent by weight or more. Examples of a solvent as another component in the aqueous solvent include water-soluble organic solvents including alcohols such as methanol and ethanol; ketones such as acetone; ethers such as tetrahydrofuran; organic acids such as acetic acid; nitriles such as acetonitrile; and aprotic polar solvents such as N,N-dimethylformamide. The concentration of water in the system for hydrothermal treatment is, for example, 20 percent by weight or more, preferably 30 percent by weight or more, more preferably 50 percent by weight or more, and particularly preferably 60 percent by weight or more. The temperature of hot water is generally 50° C. or higher, preferably 100° C. or higher, more preferably 150° C. or higher, particularly preferably 200° C. or higher, and especially preferably 250° C. or higher. The hot water may be used in a gaseous state (water vapor) or in a supercritical state.

The hydrothermal treatment may be carried out in the form of a solution or in the form of a slurry (dispersion). The article to be treated may be added in the form of a solid, a solution, or a dispersion to water.

An acid and/or a base may be used in the hydrothermal treatment. Examples of the acid include inorganic acids such as hydrochloric acid, sulfuric acid, nitric acid, phosphoric acid, and boric acid; and organic acids such as p-toluenesulfonic acid. The base can be an inorganic or organic base. Examples of such bases include alkali metal hydroxides such as sodium hydroxide and potassium hydroxide; alkaline earth metal hydroxides such as magnesium hydroxide; alkali metal carbonates such as sodium carbonate; alkaline earth metal carbonates such as calcium carbonate; alkali metal hydrogen carbonates such as sodium hydrogen carbonate; alkali metal alkoxides such as sodium methoxide and sodium ethoxide; organic acid salts of alkali metals, such as sodium acetate; amines such as triethylamine; and nitrogen-containing aromatic compounds such as pyridine.

The hydrothermal treatment may be carried out under an oxidative condition or a reductive condition. A treatment time can be appropriately set according typically to the type of article to be treated and treating temperature.

As a result of the hydrothermal treatment, the compound having a dicarboximide skeleton represented by Formula (i') is decomposed into a low-molecular-weight compound, such as carbon dioxide, ammonia, nitrogen, nitrogen dioxide, hydroxylamine, or an O-substituted hydroxylamine; and/or a compound highly soluble in water, such as a carboxylic acid or an amine.

The separation and removal of a decomposed product after the hydrothermal treatment can be carried out, for example, through stripping, bubbling, crystallization, precipitation, filtration, distillation, extraction, rinsing, and/or repulping. A decomposed product in the form of gas can be separated and removed, for example, through stripping and/or bubbling, and a decomposed product in another form can be separated and removed, for example, through crystallization, precipitation, filtration, distillation, extraction, rinsing, and/or repulping. These procedures may be performed according to a common procedure. When a decomposed product is separated and removed through crystallization, for example, a target compound with high purity from which impurities have been removed can be recovered by carrying out a crystallization procedure using a poor solvent of one of the target compound and the decomposed product. When the target compound and a decomposed product are separated through extraction, they can be separated from each other by carrying out an extraction procedure using two or more solvents that are separable from each other.

According to the present invention, impurities derived from a catalyst, particularly nitrogen-containing impurities, can be efficiently removed from a reaction product of the reaction of a substrate by the catalysis of a cyclic imide compound and/or a cyclic acylurea compound. Thus, an organic compound containing less impurities can be easily obtained. The resulting organic compound can be used, for example, as a raw material for polymers such as polyesters, polyamides, and polyimides, and as an intermediate material for fine chemicals.

EXAMPLES

The present invention will be illustrated in further detail with reference to several examples below, which, however, are by no means intended to limit the scope of the present invention. In the following examples, the nitrogen contents in crystals were analyzed and determined by a Kjeldahl decomposition method (indophenol method).

Example 1

A reaction was carried out according to a gas-liquid continuous reaction system using a reactor equipped with a reflux condenser, a stirrer, a massflow meter, a material feed line, a gas supply line, a reaction mixture extraction line, an exhaust gas line, a pressure gage, and a pressure adjuster. Specifically, the reaction was performed under conditions of a temperature of 170° C., a pressure of 2 MPa and a residence time of 2 hours while an acetic acid mixture was continuously fed to the reactor and air was continuously introduced to the reactor through the bottom thereof so that an oxygen concentration in the exhaust gas line fell within the range from 3% to 6%, and a reaction mixture was continuously discharged out of the reaction system. The acetic acid mixture to be fed contained 10 percent by weight of p-xylene, 0.5 percent by weight of N,N',N''-trihydroxyisocyanuric acid, 0.23 percent by weight of manganese(II) acetate tetrahydrate, and 0.09 percent by weight of cobalt(II) acetate tetrahydrate. The obtained reaction mixture was cooled to room temperature to precipitate crystals, and the crystals were collected through filtration. The crystals were repulped by adding acetic acid in an amount as much as ten times that of the crystals, and stirring the mixture at 60° C. for one hour. The repulped crystals were filtrated, dried, and thereby yielded crystals of terephthalic acid. A hydrothermal treatment was then conducted by adding water in an amount as much as ten times by weight that of the crystals to the crystals and stirring the mixture at 300° C. for one hour. The mixture was cooled to 60° C., and crystals were filtrated and dried. The resulting crystals had a nitrogen content of 15 parts per million by weight. In this connection, the crystals before hydrothermal treatment had a nitrogen content of 140 parts per million by weight and contained isocyanuric acid.

Example 2

The procedure of Example 1 was performed, except for carrying out a hydrothermal treatment at 60° C. for one hour. The crystals after the hydrothermal treatment had a nitrogen content of 130 parts per million by weight.

Example 3

In an autoclave were placed 0.21 g of isocyanuric acid and 149.79 g of water, followed by stirring at 300° C. for one hour. After being cooled, the reaction mixture was analyzed by high-performance liquid chromatography (HPLC) to find that no isocyanuric acid was detected.

Example 4

In an autoclave were placed 0.21 g of isocyanuric acid, 134.81 g of water, and 14.98 g of acetic acid, followed by stirring at 300° C. for one hour. After being cooled, the reaction mixture was analyzed by high-performance liquid chromatography (HPLC) to find that no isocyanuric acid was detected.

INDUSTRIAL APPLICABILITY

According to the present invention, there is provided a method for producing an organic compound by the catalysis of a catalyst including a compound having a dicarboximide skeleton and a method for decomposing a compound having a dicarboximide skeleton. According to these methods, catalyst-derived impurities can be easily or readily removed from a product of a reaction by the catalysis of the compound having a dicarboximide skeleton, and a target compound with high purity can be efficiently produced; and the compound having a dicarboximide skeleton can be efficiently decomposed.

The invention claimed is:

1. A method for producing an organic compound through a reaction of a substrate in the presence of a catalyst, the catalyst including a compound having a dicarboximide skeleton represented by following Formula (i):

[Chemical Formula 1]

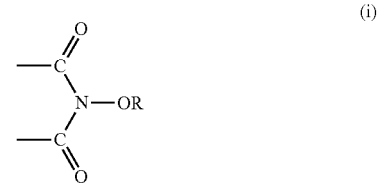

wherein R represents hydrogen atom or a hydroxyl-protecting group, the method comprising the step of hydrothermally treating products of the reaction with hot water of 300° C. or more so as to decompose and remove an impurity derived from the catalyst and included in the products;

wherein the organic compound is an addition or substitution reaction product between a radical-formable compound and a radical-scavenging compound, or a derivative of said addition or substitution reaction product derived by a reaction selected from the group consisting of an oxidation reaction, a cyclization reaction, a dehydration reaction, a decarboxylation reaction, a rearrangement reaction, and an isomerization reaction.

2. The method for producing an organic compound of claim 1, wherein the compound having a dicarboximide skeleton is a cyclic imide compound or a cyclic acylurea compound, wherein the cyclic imide compound has a cyclic imide skeleton represented by following Formula (I):

[Chemical Formula 2]

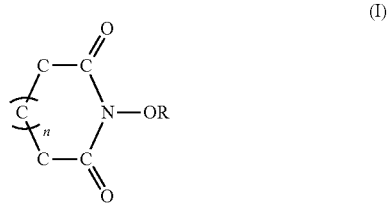

wherein "n" represents 0 or 1; and R represents hydrogen atom or a hydroxyl-protecting group, and wherein the cyclic acylurea compound has a cyclic acylurea skeleton represented by following Formula (II):

[Chemical Formula 3]

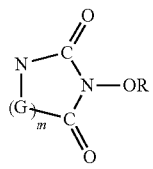
(II)

wherein "m" represents 1 or 2; G represents carbon atom or nitrogen atom, and, when "m" is 2, two Gs may be the same as or different from each other; and R is as defined above.

3. A method for decomposing a compound having a dicarboximide skeleton represented by following Formula (i'):

[Chemical Formula 4]

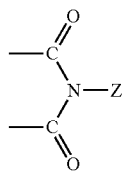
(i')

wherein Z represents hydrogen atom or an —OR group, wherein R represents hydrogen atom or a hydroxyl-protecting group, the method comprising the step of hydrothermally treating the compound with hot water of 300° C. or more so as to decompose the compound; wherein the compound having a dicarboximide skeleton is a cyclic imide compound or a cyclic acylurea compound, wherein the cyclic imide compound has a cyclic imide skeleton represented by following Formula (I'):

[Chemical Formula 5]

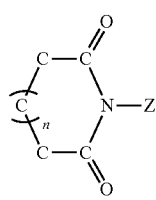
(I')

wherein "n" represents 0 or 1; Z represents hydrogen atom or an —OR group, wherein R represents hydrogen atom or a hydroxyl-protecting group, and wherein the cyclic acylurea compound has a cyclic acylurea skeleton represented by following Formula (II'):

[Chemical Formula 6]

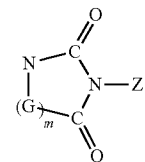
(II')

wherein "m" represents 1 or 2; G represents carbon atom or nitrogen atom, and, when "m" is 2, two Gs may be the same as or different from each other; and Z is as defined above.

* * * * *

UNITED STATES PATENT AND TRADEMARK OFFICE
CERTIFICATE OF CORRECTION

PATENT NO. : 7,994,330 B2  Page 1 of 1
APPLICATION NO. : 11/885125
DATED : August 9, 2011
INVENTOR(S) : Naruhisa Hirai et al.

It is certified that error appears in the above-identified patent and that said Letters Patent is hereby corrected as shown below:

ON THE TITLE PAGE:

At section (86), change:

"PCT No.:   PCT/JP2006/005691"

to

--PCT No.:   PCT/JP2006/305691--.

Signed and Sealed this
Twenty-second Day of November, 2011

David J. Kappos
*Director of the United States Patent and Trademark Office*